US006926864B2

(12) United States Patent
Peeters et al.

(10) Patent No.: US 6,926,864 B2
(45) Date of Patent: Aug. 9, 2005

(54) MICROFLUIDICS APPARATUS AND METHODS FOR USE THEREOF

(76) Inventors: John P. Peeters, 4607 Harling La., Bethesda, MD (US) 20814; Thomas Wiggins, 7680 Mickey's Pride, Columbia, MD (US) 21046; Madhushree Ghosh, 12782 Torrey Bluff Dr., Apt. 99, San Diego, CA (US) 92130; Lawrence A. Bottomley, 3361 Connemara Ter., Lawrenceville, GA (US) 30044; Salvatore Seminara, 1927 W. Cuyler Ave., Chicago, IL (US) 60613; Zhiyu Hu, 1611 Laurel Ave. Apt. 1015, Knoxville, TN (US) 37916; Timothy Seeley, 8116 Old Georgetown Rd., Bethesda, MD (US) 20814; Sebastian Kossek, 3901 E. Hidden View Dr., Phoenix, AZ (US) 85048

( * ) Notice: Subject to any disclaimer, the term of this patent is extended or adjusted under 35 U.S.C. 154(b) by 424 days.

(21) Appl. No.: 10/054,760

(22) Filed: Nov. 13, 2001

(65) Prior Publication Data

US 2003/0092016 A1 May 15, 2003

Related U.S. Application Data

(63) Continuation-in-part of application No. 10/036,733, filed on Nov. 9, 2001, now abandoned.

(51) Int. Cl.[7] .................. G01N 15/06; G01N 33/00; G01N 33/48; G01N 30/96; G01N 27/00
(52) U.S. Cl. ................ 422/68.1; 422/50; 422/69; 422/81; 422/82; 422/82.01; 435/283.1; 435/287.1; 435/287.3; 435/288.4; 435/288.5; 436/43; 436/63
(58) Field of Search ............... 422/50, 68.1, 69, 422/81, 82, 82.01; 435/283.1, 287.1, 287.3, 288.4, 288.5; 436/43, 63

(56) References Cited

U.S. PATENT DOCUMENTS

| | | | |
|---|---|---|---|
| 5,653,939 A | | 8/1997 | Hollis et al. |
| 5,763,768 A | | 6/1998 | Henderson et al. |
| 5,807,758 A | | 9/1998 | Lee et al. |
| 5,923,421 A | | 7/1999 | Rajic et al. |
| 5,992,226 A | | 11/1999 | Green et al. |
| 6,016,686 A | | 1/2000 | Thundat |
| 6,041,642 A | | 3/2000 | Duncan |
| 6,050,722 A | | 4/2000 | Thundat et al. |
| 6,054,277 A | * | 4/2000 | Furcht et al. ............ 435/6 |
| 6,096,559 A | | 8/2000 | Thundat et al. |
| 6,118,124 A | | 9/2000 | Thundat et al. |
| 6,123,819 A | | 9/2000 | Peeters |
| 6,485,690 B1 | * | 11/2002 | Pfost et al. .......... 422/102 |
| 6,523,392 B2 | * | 2/2003 | Porter et al. ......... 73/24.01 |
| 6,620,625 B2 | * | 9/2003 | Wolk et al. .......... 436/180 |

FOREIGN PATENT DOCUMENTS

WO  WO 00/66266  5/2000

OTHER PUBLICATIONS

Thundat et al. (1997). *Microscale Thermophysical Engineering 1*: 185–199.

* cited by examiner

*Primary Examiner*—Jill Warden
*Assistant Examiner*—Brian Sines

(57) ABSTRACT

A microfluidics device includes a plurality of interaction cells and fluid control means including i) means for providing to the interaction cells a preparation fluid, and ii) means for providing to the interaction cells a sample fluid, wherein each interaction cell receives a different sample fluid. A plurality of microcantilevers may be disposed in each of the interaction cells, wherein each of the plurality of microcantilevers configured to deflect in response to an interaction involving a component of the sample fluid.

26 Claims, 20 Drawing Sheets

US 6,926,864 B2

MICROFLUIDICS APPARATUS AND METHODS FOR USE THEREOF

The present application is a continuation-in-part of the application Ser. No. 10/036,733 entitled "Microfluidics Apparatus and Methods of Use Therefor" which was filed in the United States Patent and Trademark Office on Nov. 9, 2001 now abandoned, and which is incorporated herein by reference.

GOVERNMENT FUNDING

A portion of the invention was made with funding from the Department of Energy. The government has certain rights in the invention.

TECHNICAL FIELD

The present invention relates to chemical analysis, and in particular to methods and apparatuses for performing chemical analysis of biomaterials with a microfluidics device using microcantilevers.

BACKGROUND OF THE INVENTION

It is known that thin bimorph microcantilevers can undergo bending (deflection) due to differential stresses following exposure to and binding of a compound from their environment, for example in a fluid sample. Soft microcantilevers having spring constants less than 0.1 N/m are sensitive to stress differentials that arise as a result of interactions between extremely small amounts of a substrate material on a surface of the microcantilever and one or more materials in a sample. For a given microcantilever with a specially designed coating layer, the deflection yields information about components of the environment to which the microcantilever is exposed.

Microcantilevers are capable of detecting calorimetric enzyme-mediated catalytic biological reactions with femto-Joule resolution. (Thundat et al., "Microcantilever Sensors", Microscale Thermophysical Engr. 1, pgs. 185–199, 1997.) Further, oligonucleotide interactions within a sample can be detected using a monolithic array of test sites formed on a surface to which the sample is applied as shown in U.S. Pat. No. 5,653,939.

It is also known to provide integrated chips to categorize molecules in a biochemical sample. For example, U.S. Pat. No. 6,123,819 to Peeters discloses a design for an integrated chip having an array of electrodes at the atomic or nano scale. The chip can be used to characterize single molecules in a solution such as individual proteins, complex protein mixtures, DNA, or other molecules.

In recent years, microfludics technology employing microcantilevers has emerged to provide a "lab-on-a-chip" for chemical analysis of biomaterials. For example, U.S. Pat. No. 6,054,277 to Furcht et al. discloses a genetic testing system that includes an integrated, unitary microchip-based detection device with microfluidic controls. The device employs a microcantilever sensor to detect a biochemical reaction in a single detection chamber having capillary interconnects. However, to analyze a number of solutions simultaneously, it would be necessary to utilize an equal number of these chips

SUMMARY OF THE INVENTION

In one embodiment, a microfluidics device is provided. The microfluidics device comprises a plurality of interaction cells and fluid control means, including: i) means for providing to the interaction cells a preparation fluid, and ii) means for providing to the interaction cells a sample fluid, wherein each interaction cell receives a different sample fluid. In a related embodiment, a plurality of microcantilevers is disposed in each of the interaction cells, each of the plurality of microcantilevers being configured to deflect in response to an interaction involving a component of the sample fluid. The fluid control means may include means for removing a fluid from the interaction cells. The fluid control means may be robotic or it may be manual. Additionally, the plurality of microcantilevers may be provided as a plurality of fingers in a planar array. In accordance with another related embodiment, the microfluidics device is disposable. In another related embodiment, the microfluidics device is reusable.

In accordance with another embodiment, a microcantilever platform includes a plurality of interaction cells, each of the interaction cells including an inlet for receiving a sample fluid, wherein each of the interaction cells receives a different sample fluid; at least one microcantilever is disposed in each of the interaction cells, the microcantilever being capable of deflecting in response to chemical interaction with a component of the sample fluid. In related embodiments, each interaction cell further includes at least one outlet whereby fluid may flow out of the cell. The microcantilever platform may be disposable or reusable.

In accordance with a further embodiment, an apparatus is provided for performing microfluidics analysis, which apparatus includes a housing comprising a plurality of fluid lines; each of the fluid lines includes an inlet for receiving a fluid from a fluid pump and a plurality of control lines in communication with the fluid lines, each of the control lines including an inlet for receiving a control fluid; the apparatus also includes a microfluidics device having a plurality of interaction cells, each of the interaction cells including an inlet for receiving one or more preparation fluids and a sample fluid, and wherein each of the interaction cells receives a different sample fluid; each of the interaction cells also includes an outlet whereby fluid may flow out of the interaction cell; each of the interaction cells may also include at least one microcantilever configured to deflect in response to chemical interactions with a component of the sample fluid; and the apparatus further includes a plurality of valves in communication with the fluid lines for controlling the flow of fluid into and out of the interaction cells.

The apparatus may further include a plurality of microcantilevers disposed in each interaction cell, and the plurality of microcantilevers may be provided in a planar array having a plurality of fingers. In accordance with related embodiments, the control fluid is a gas. The number of the plurality of valves may be less than the number of the plurality of fluid lines. Similarly, the number of the plurality of valves may be less than the number of the plurality of control lines. In accordance with further related embodiments, the apparatus is mounted on a temperature-controlled platform.

The apparatus may also include a plurality of expansion chambers for eliminating gas from fluid entering the interaction cells, and/or a waste receptacle for receiving fluid from the outlets of the interaction cells. In accordance with further related embodiments, the apparatus may also include a reservoir for sample collection from each outlet of each interaction cell, and the sample collected in at least one of the reservoirs may be subject to further analysis. The further analysis may include gel electrophoresis, for example, the gel electrophoresis may be multi dimensional. At least one of the dimensions may be polyacrylamide gel electrophoresis in the presence of a denaturing detergent. The further analysis may also include mass spectroscopy.

In accordance with another embodiment, a method is provided for identifying an analyte in a plurality of sample fluids. The method includes causing a preparation solution to flow into one or more of a plurality of interaction cells, wherein each of the interaction cells includes at least one microcantilever, and the preparation fluid includes a ligand that binds to the microcantilever and has affinity for the analyte; at least one sample solution flows into the one or more interaction cells, and a deflection of the microcantilever in each interaction cell having sample solution containing the analyte is detected.

In accordance with related embodiments, causing the preparation solution to flow into one or more of the plurality of interaction cells further includes causing a linker solution to flow into one or more of the interaction cells, wherein the linker solution is capable of binding the ligand to the microcantilever. Causing the preparation solution to flow into one or more of the plurality of interaction cells may further include causing a wash solution to flow into one or more of the interaction cells. Additionally, causing a preparation solution to flow into one or more of the plurality of interaction cells also includes causing a receptor solution to flow into one or more of the interaction cells and/or causing a buffer solution to flow into one or more of the interaction cells. In accordance with related embodiments, the method may include mounting the interaction cells on a temperature-controlled platform.

In accordance with further related embodiments, the number of sample solutions may equal the number of interaction cells. Similarly the number of sample solutions may be less than the number of interaction cells. The ligand may be selected from a group consisting of a protein and a nucleic acid, and the nucleic acid may be RNA or DNA. The protein may be may be an epitope, an enzyme, or a polypeptide, and the analyte may be selected from a group consisting of all or a portion of a nucleic acid and a protein. The analyte may also be a hormone, and the hormone may be selected from a group consisting of a steroid and a polypeptide. In another related embodiment, the ligand and the analyte are each selected from a group consisting of an antibody and an antigen.

In accordance with yet another embodiment of the invention, microfluidics device includes a housing comprising a plurality of fluid lines. Each of the fluid lines includes an inlet for receiving a fluid from a fluid pump disposed within the housing. The housing also includes a plurality of control lines in communication with the fluid lines, wherein each of the control lines includes an inlet for receiving a control fluid. The embodiment also includes a microcantilever platform having a plurality of interaction cells. Each of the interaction cells includes an inlet for receiving one or more preparation fluids and a sample fluid and an outlet whereby fluid may flow out of the interaction cell. Additionally, each of the interaction cells receives a different sample fluid. A plurality of valves is in communication with the fluid lines for controlling the flow of fluid into and out of the interaction cells.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
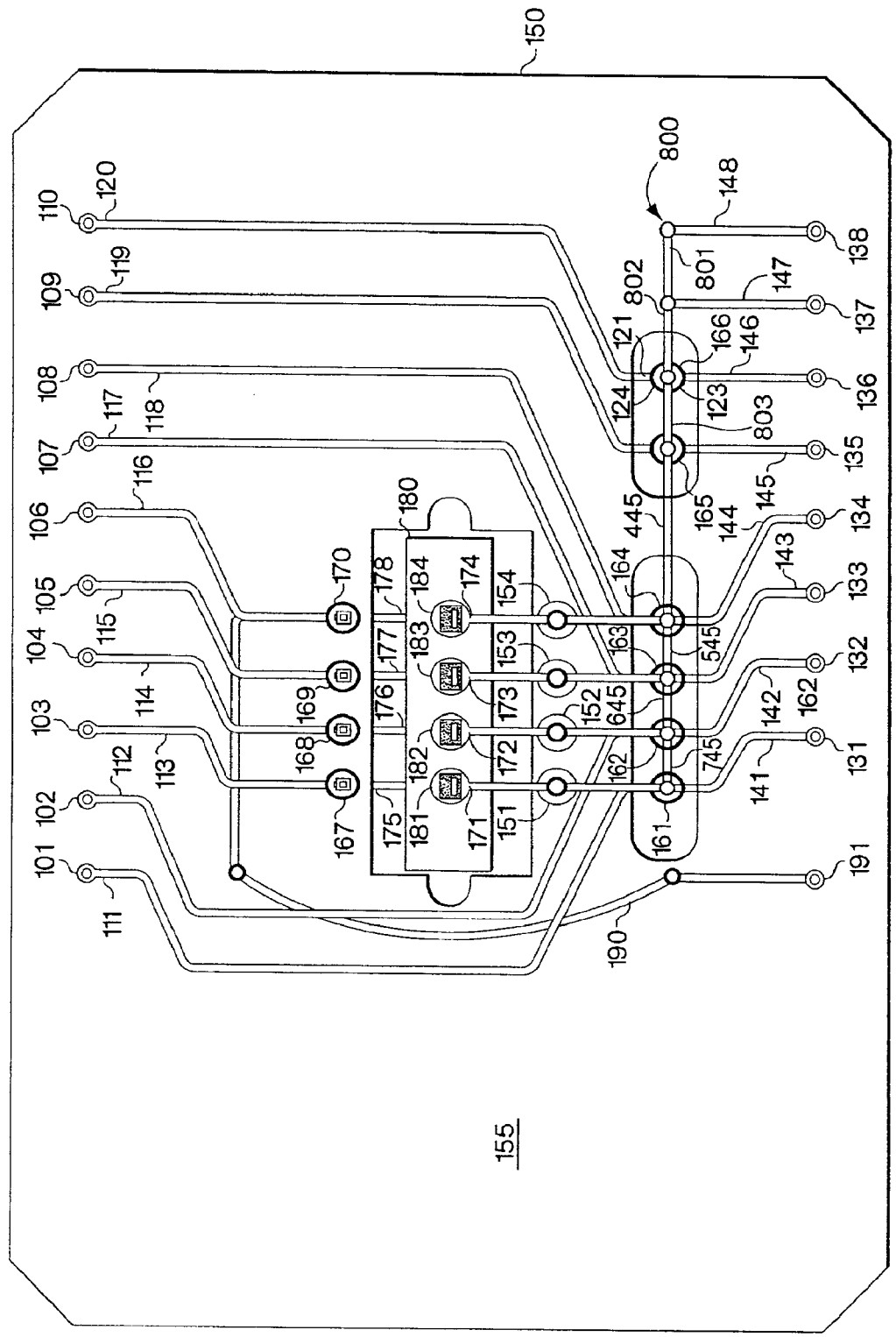
FIG. 1 is a graphical illustration showing a top view of an apparatus for performing microfluidic analysis in accordance with an embodiment of the invention.

FIG. 1 is a graphical illustration showing a top view of an apparatus for performing microfluidic analysis in accordance with an embodiment of the invention. The apparatus includes three dimensional a housing 150 having a plurality of fluid lines 141–148. The fluid lines 141–148 are disposed within the housing in at least two layers such that some fluid lines are closer to a top face of the housing 155 and others are closer to a bottom face of the housing 156, shown in FIG. 2. Each of the fluid lines has an inlet 131–138 for receiving a fluid from a fluid pump or other fluid delivery apparatus. Such a fluid pump may be external to the housing 150 or it may be part of the housing so as to create a completely self-contained unit. The housing 150 also includes a plurality of control lines 111–120 in communication with valves 161–170. Valves 161–166 are in communication with the fluid lines 141–148. Each of the control lines 111–120 receives a control fluid, such as a gas or other fluid, from an inlet 101–110. The fluid lines 141–148, control lines 111–120 and fluid paths (discussed below) may be about 0.5 mm in diameter. For example, the diameter of the lines and paths may range from about 0.05 mm to about 0.6 mm. In accordance with further embodiments of the invention, the diameter of the lines and paths may be about 0.05 mm to about 0.2 mm; from about 0.1 mm to about 0.3 mm; and from about 0.2 mm to about 0.6 mm. Control fluid and other fluids may be provided to the apparatus through the use of a robotic device, or may be provided manually.

Figure 2:
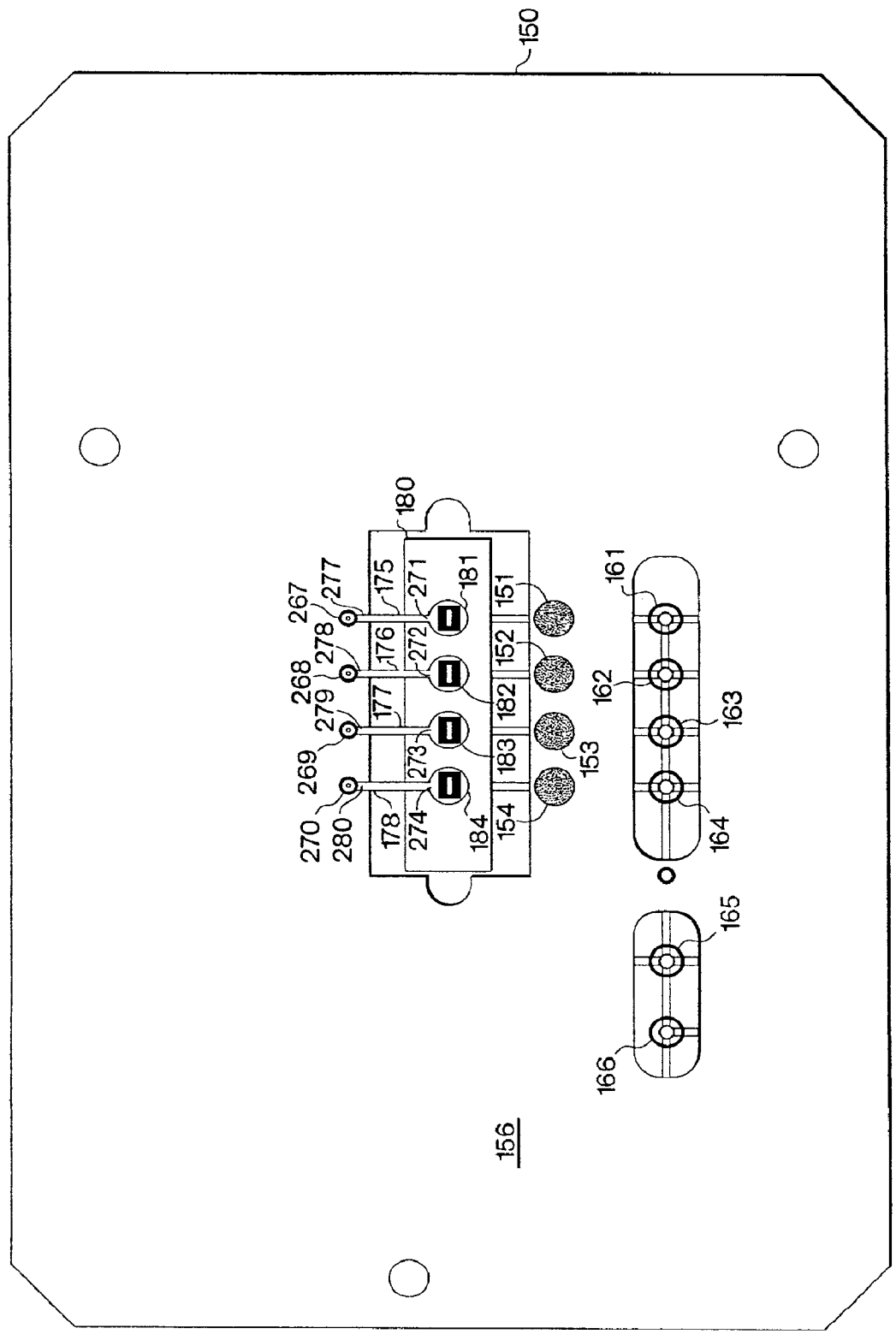
FIG. 2 is a graphical illustration showing a bottom view of the apparatus of FIG. 1.

A plurality of valves 161–170 control the flow of fluid into and out of a microcantilever platform 180. In this embodiment, the valves 161–166 are two-way valves that communicate with the fluid lines 141–148. The valves 161–166 all lead to a common line or manifold 800 comprising fluid paths 801–803 and 445, 545, 645, and 745, and each valve has an input and an output. For example, valve 166 has an input 121 for receiving control fluid from control line 120 and an output 124 that permits fluid to flow both from fluid line 146 and fluid path 802. In other words, valve 166 controls the output of fluid line 146 as well as the output of fluid path 802, which runs under fluid line 146. As shown in FIG. 2, valves 167–170 are also two way valves and each of these has a valve inlet 267–270 and a valve outlet 277–280. In order for fluid to flow though the housing, at least one of valves 167–170 must be open.

The valves 161–170 may be pneumatic valves that are activated by the control fluid. In the embodiments of FIGS. 1–14, the control fluid, when pressurized, serves to close the valves 161–170. In FIG. 1 the control fluid has not been pressurized, thus the valves are all open, whereas in FIG. 3, the control fluid is pressurized and the valves 161–170 are closed. When the control fluid is a high density gas, such as air, the response time of the valves quickens. The number of valves in the apparatus may be less than, more than or equal to the number of fluid lines. Similarly, the number of valves may be less than, equal to or more than the number of control lines.

The microcantilever platform 180 is disposed in the housing 150 and includes a plurality of interaction cells 181–184. Each of the interaction cells 181–184 has an inlet 171–174 for receiving one or more preparation fluids and a sample fluid and an outlet, 271–274 as shown in FIG. 2, for releasing fluid from the cell through output lines 175–178. The interaction cells may be about 4 mm in diameter. For example, the diameter of the interaction cells may range from about 0.5 mm to about 6 mm. In accordance with further embodiments of the invention, the diameter of the interaction cells may range from about 0.5 mm to about 2.5 mm; from about 1 mm to about 3 mm; from about 2 mm to about 5 mm; or from about 3 mm to about 6 mm.

In accordance with an embodiment of the invention, the microcantilever platform 180 is a micro-mechanical system wherein each of the interaction cells includes at least one microcantilever configured to deflect in response to interactions with a chemical component of the sample fluid. Alternatively, each of the interaction cells 181–184 may include a plurality of microcantilevers provided in a planar array of fingers.

As used herein, the term "microcantilever" is a structural term that refers to a flexible beam that may be bar-shaped, V-shaped, or have other shapes, depending on its application. One end of the microcantilever may be fixed on a supporting base with another end standing freely. Microcantilevers are usually of microscopic dimensions, for example, they can be about 50 $\mu$m to about 750 $\mu$m in length. In accordance with an embodiment of the invention, the microcantilevers are preferably 200 $\mu$m to 700 $\mu$m in length, more preferably 250 $\mu$m to 600 $\mu$m in length, and most preferably 300 $\mu$m to 500 $\mu$m in length. Further, the width can be, for example, about 50 $\mu$m to about 300 $\mu$m. Each microcantilever may be from about 0.5 $\mu$m to about 4.0 $\mu$m thick. Silicon and silicon nitride are the most common molecules used to fabricate microcantilevers. However, other molecules may be used for making microcantilevers, including piezoelectric molecules, plastic molecules and various metals.

In accordance with embodiments of the invention, the microcantilevers can be manufactured from ceramics, silicon, silicon nitride, other silicon compounds, metal compounds, gallium arsenide, germanium, germanium dioxide, zinc oxide, diamond, quartz, palladium, tantalum pentoxide, and plastic polymers. Plastics can include: polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, and polythiophene. Microcantilevers that are custom fabricated may be obtained from, for example, Diffraction Ltd., Waitsfield, Vt. Further, U.S. Pat. Nos. 6,096,559 issued Aug. 1, 2000, and 6,050,722 issued Apr.18, 2000, describe fabrication of a microcantilever, including use of material such as ceramics, plastic polymers, quartz, silicon nitride, silicon, silicon oxide, aluminum oxide, tantalum pentoxide, germanium, germanium dioxide, gallium arsenide, zinc oxide, and silicon compounds.

Microcantilevers that can be employed in accordance with the invention may have a compound immobilized on the surface of a free end to detect and screen receptor/ligand interactions, antibody/antigen interactions and nucleic acid interactions as is disclosed in U.S. Pat. No. 5,992,226, issued on Nov. 30, 1999. Microcantilevers can be used to detect enzyme activities directed against a substrate located on a surface of the microcantilever. Deflection may be measured using either of optical or piezoelectric methods. Further, the microcantilevers of the embodiments of the invention can measure concentrations using electrical methods to detect phase difference signals that can be matched with natural resonant frequencies as shown in U.S. Pat. No. 6,041,642, issued Mar. 28, 2000. Determining a concentration of a target species using a change in resonant properties of a microcantilever on which a known molecule is disposed, for example, a biomolecule selected from DNA, RNA, and protein, is described in U.S. Pat. No. 5,763,768.

In accordance with embodiments of this invention, a method and apparatus for detecting and measuring physical and chemical parameters in a sample media may use micromechanical potentiometric sensors as disclosed in U.S. Pat. No. 6,016,686, issued Jan. 25, 2000. Chemical detection of a chemical analyte is described in U.S. Pat. No. 5,923,421, issued Jul. 13, 1999. Further, magnetic and electrical monitoring of radioimmune assays, using antibodies specific for target species which cause microcantilever deflection (e.g., magnetic beads binding the target to the microcantilever, as described in U.S. Pat. No. 5,807,758, issued Sep. 15, 1998) would be consistent with embodiments of the invention.

The term "first surface" as used herein refers to that geometric surface of a microcantilever designed to receive and bind to a ligand and further to an analyte. One or more coatings can be deposited upon this first surface. The term "second surface" refers to the area of the opposite side of the microcantilever that is designed not to receive the ligand or bind to the analyte. As the second surface is generally not coated, it is generally comprised of the material from which the microcantilever or microcantilever array is fabricated, prior to any coating procedure applied to the first surface. Alternatively, it may be coated with a material different from the first surface's coating.

Coating of micromechanical sensors with various interactive molecules is described in U.S. Pat. No. 6,118,124, issued Sep. 12, 2000. A coating material is deposited on a microcantilever by depositing a metal which may be selected from at least one of the group consisting of aluminum, copper, gold, chromium titanium, and silver. Further, a plurality of metals may be deposited on a microcantilever by depositing, for example, a first layer of chromium and a second layer of gold, or a first layer of titanium and a second layer of gold. Coatings may be amalgams or alloys comprising a plurality of metals.

In accordance with embodiments of the invention, a first surface of a microcantilever can be fabricated to have an intermediate layer, for example, sandwiched between the first surface comprising for example, gold, and the second surface, comprising for example silicon nitride. The intermediate layer may be an alloy comprising a plurality of metals. For example, the intermediate layer may be an amalgam comprising mercury with at least one of chromium, silver, and titanium.

A microcantilever may deflect or bend from a first position to at least a second position due to differential stress on a first surface of the microcantilever in comparison to a second surface. That is, a microcantilever may deflect in response to the change in surface stress resulting from exposure of the microcantilever to a component of a particular environment. A microcantilever may also deflect in response to a change in the environment. A change in the environment may occur as the result of adding a sample having or lacking an analyte, having a higher or lower analyte concentration, adding or omitting a specific co-factor of an analyte, having a higher or lower concentration of the co-factor, having or lacking a specific inhibitor of an analyte, or having a higher or lower concentration of an inhibitor. Further, a sample may be diluted or concentrated and a solution may experience a change in temperature, pH, conductivity or viscosity prior to, during or after exposure to a microcantilever.

When one end of a microcantilever is fixed to a supporting base as described above, deflection is measured by measuring a distance the distal end of the microcantilever (i.e., the end distal to the end fixed to the supporting base) has moved. The distal end may move from a first position to a second position. In the first position, the biomaterial on the first surface of the microcantilever has not yet bound to or reacted with the analyte. In the second position, the biomaterial on the microcantilever has bound to or has reacted with the analyte in the environment.

A "deflection characteristic", as used herein, is a pattern of deflection of a microcantilever that is reproducible in extent of distance traveled, for example as measured in nm, and frequency per unit time. The deflection characteristic can distinguish specific conditions of ligand and analyte, and further reaction conditions such as temperature, concentration, ionic strength, presence of cation or other co-factors, preservatives, and other conditions well known to one of the chemical arts. The deflection under these conditions thereby can become a signature for the specific reaction. A deflection characteristic is calculated from a measurement of movement of the microcantilever upon addition of a sample, or measurement of movement as a function of concentration of an analyte, a ligand, an inhibitor, or a co-factor. A deflection characteristic may also be calculated as a function of pH, or of temperature, and the like.

Each of the interaction cells 181–184 may receive a different sample fluid as will be discussed in more detail below. A microprocessor can be included in an apparatus or a method, such that an integrated circuit containing the arithmetic, logic, and control circuitry required to interpret and execute instructions from a computer program may be employed to control activation of the the valves. Further, microprocessor components of the measuring devices may reside in an apparatus for detection of microcantilever deflection.

Figure 20:
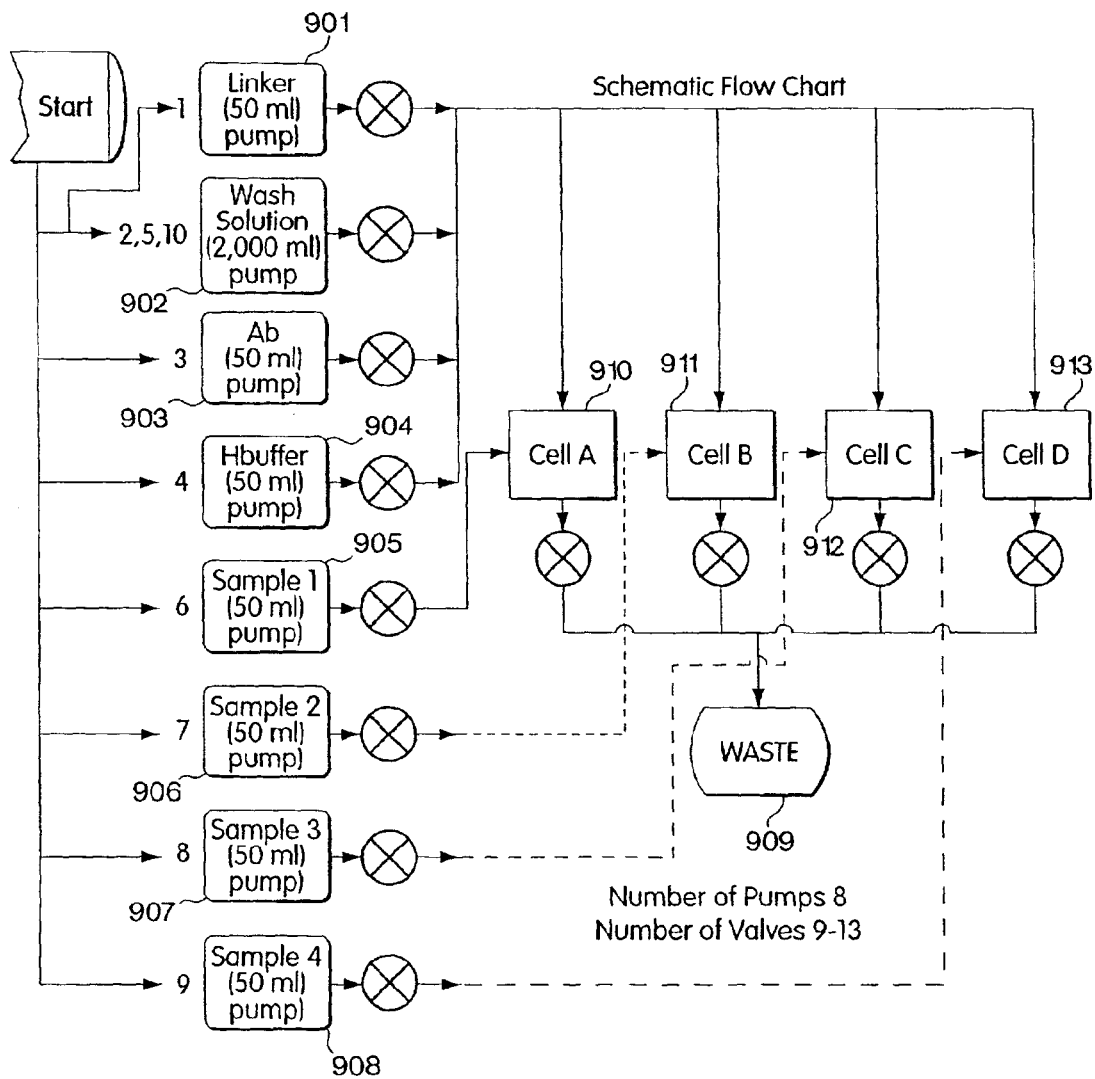
FIG. 20 is a schematic flow chart illustrating a fluidics system for use in accordance with a method for identifying an analyte in a plurality of sample fluids in accordance with a further embodiment of the invention.

The apparatus may also include a plurality of expansion chambers 151–154 for eliminating gas from fluids entering the interaction chamber 181–184, and a waste line 190 with a waste outlet 191 for releasing waste from the interaction cells 181–184 into a waste receptacle (item 909 in FIG. 20). Further, each interaction cell 181–184 may be in fluid communication with its own waste receptacle or with a reservoir for collecting the contents of the interaction cell in order to perform further analysis on what is contained in the reservoir. Further analysis may include gel electrophoresis, and the gel electrophoresis may be multi-dimensional. Additionally, at least one of the dimensions may be polyacrylamide gel electrophoresis in the presence of a denaturing detergent. Further analysis may also include mass spectroscopy.

The apparatus of FIGS. 1 and 2 may be a card or cartridge consisting of about 17 layers of one more plastic polymers. Such cards and cartridges may be custom manufactured, for example, by Micronics, Inc. of Redmond, Wash. These cards or cartridges may be mounted in a manifold that receives fluid pump lines or fluid from other fluid delivery devices. Similarly, the pumps may be part of the card as mentioned above. The apparatus may also be mounted on a temperature-controlled platform. The apparatus may be used to identify a particular molecule in one or more sample fluids, as is shown in FIGS. 3–14.

Figure 3:
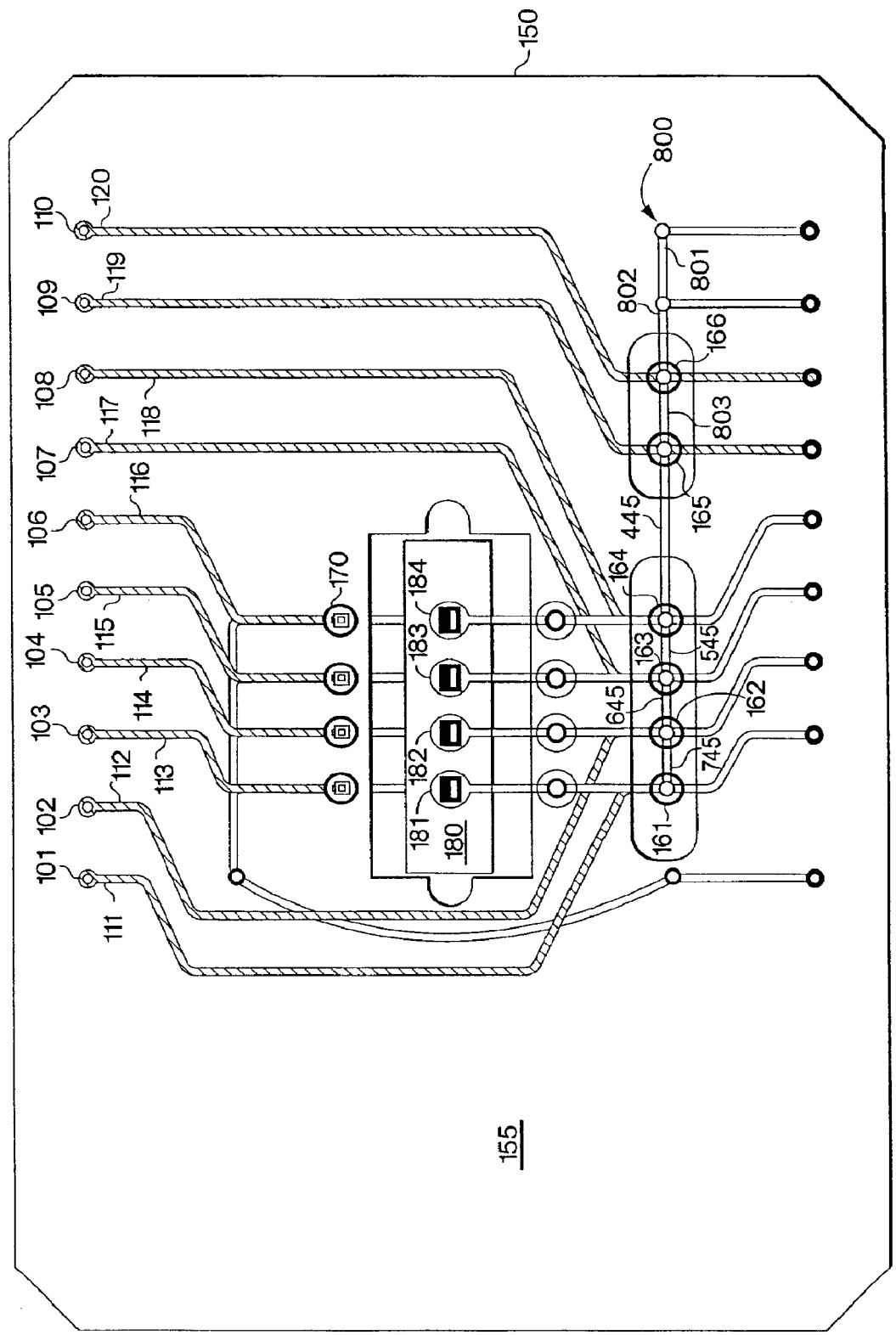
FIG. 3 is a graphical illustration of the embodiment of FIG. 1 showing all valves closed.

In FIG. 3, a control fluid, in this case a gas such as air, is pressurized in the control lines 111–120 through the inlets 101–110 to close the valves 161–170. When all the valves have been closed, fluid cannot flow into or out of the interaction cells. Thus, all of the valves are initially closed (by pressurizing a control fluid in the control lines) and then opened (by de-pressurizing the control fluid) to allow liquid to flow into appropriate interaction cells. This is done so that preparation fluids, such as linker, buffer, ligand solutions, and sample solutions containing an analyte may be input to the interaction cells 181–184 in a discriminatory manner. For example, a buffer solution may be input to all of the cells or to a subset of the cells, for example, to three of the cells, two of the cells or only to one of the cells. Similarly, a different sample solution may be input to each of the cells, or to a subset of the cells.

Figure 4:
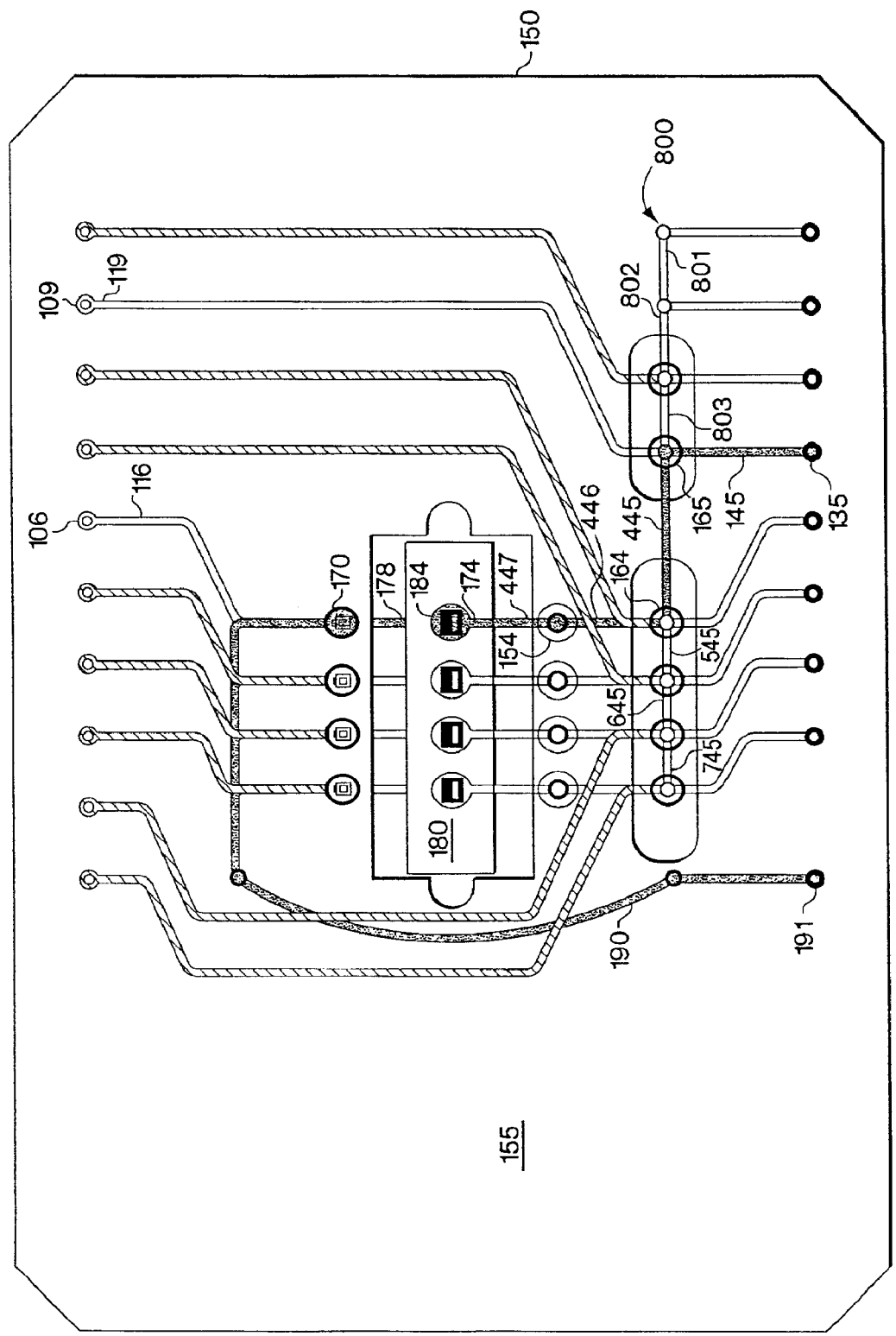
FIG. 4 is a graphical illustration of the embodiment of FIG. 1 showing a linker solution added to a first interaction cell.

FIG. 4 shows a linker solution being added to a first interaction cell. The term "linker solution" may include the following compounds: dithiobis(succinimidyl-undecanoate) (DSU), which can be purchased from Pierce Endogen, Inc. (Rockford, Ill.); long chain succinimido-6[3-(2-pyridyldithio)-propionamido]hexanoate (LCSPDP), which contains pyridyldithio and NHS ester reactive groups that react with sulfhydryl and amino groups and can be purchased from Pierce; succinimidyl-6[3-(2-pyridyldithio)-propionamido]hexanoate (SPDP), which contains pyridyldithio and NHS ester reactive groups that react with sulfhydryl and amino groups and can be purchased from Pierce; and m-maleimidobenzoyl-N-hydroxysuccinimide ester (MBS), which contains NHS ester and maleimide reactive groups that react with amino and sulfhydryl groups, and can be purchased from Pierce.

To add linker to the first interaction cell, inlets 109 and 106 do not receive the control gas, thus no control gas is input to control lines 119 and 116, and valves 165 and 170 are opened. The linker solution flows from a fluid pump or other fluid delivery device to inlet 135 into fluid line 145. Since valve 165 is open, the fluid may then flow through fluid path 445 into fluid path 446, and into expansion chamber 154. Gas may optionally be eliminated from the linker solution in the expansion chamber 154, and the linker solution flows through fluid path 447 into interaction cell 184 via inlet 174. Any outflow of fluid from the interaction cell 184 will flow into output line 178, and because valve 170 is open, the outflow will be stored in a waste receptacle (or in a reservoir for collection) via fluid waste line 190 and waste outlet 191.

Figure 5:
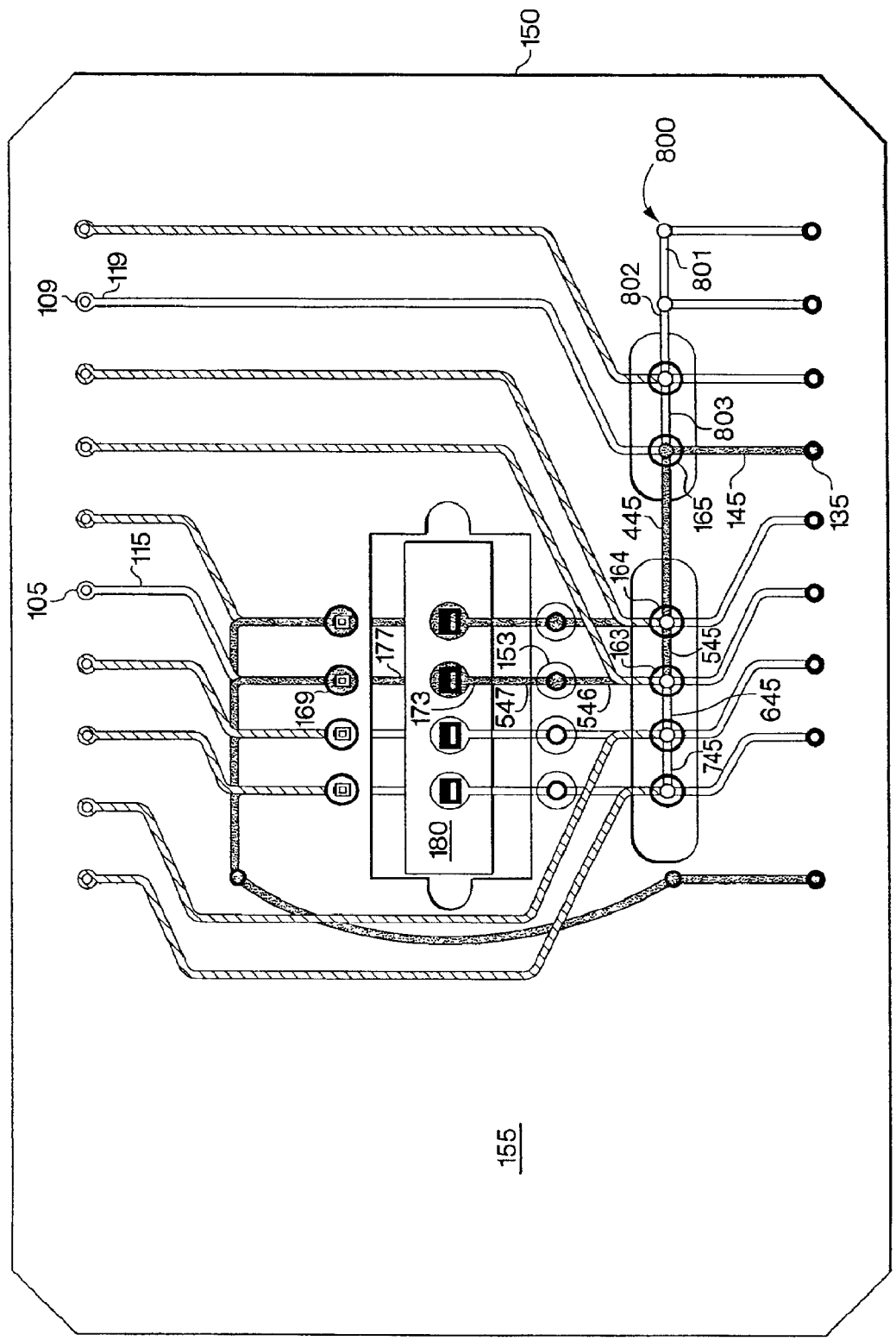
FIG. 5 is a graphical illustration of the embodiment of FIG. 1 showing a linker solution added to a second interaction cell.

FIG. 5 illustrates how the linker solution may be added to the second interaction cell, while keeping all other interaction cells isolated, by pressurizing the control fluid in all control lines except control lines 115 and 119, thus opening valves 165 and 169. As above, the linker solution flows from a fluid pump to inlet 135 into fluid line 145 and then through fluid paths 445 and 545. Note that the control lines 111, 112, 117, and 118 intersect fluid lines 141, 142, 143 and 144 respectively at a point above valves 161–164. Consequently, fluid may flow from fluid path 445 to 545 in a relatively unrestricted manner. At this point the fluid will flow into fluid path 546, and then into expansion chamber 153. Gas is eliminated from the linker solution in the expansion chamber 153, and the linker solution flows through fluid path 547 into interaction cell 183 via inlet 173. Any outflow of fluid from the interaction cell 183 will flow into output line 177, and because valve 169 is open, the outflow will be stored in a waste receptacle via fluid waste line 190 and waste outlet 191.

Figure 6:
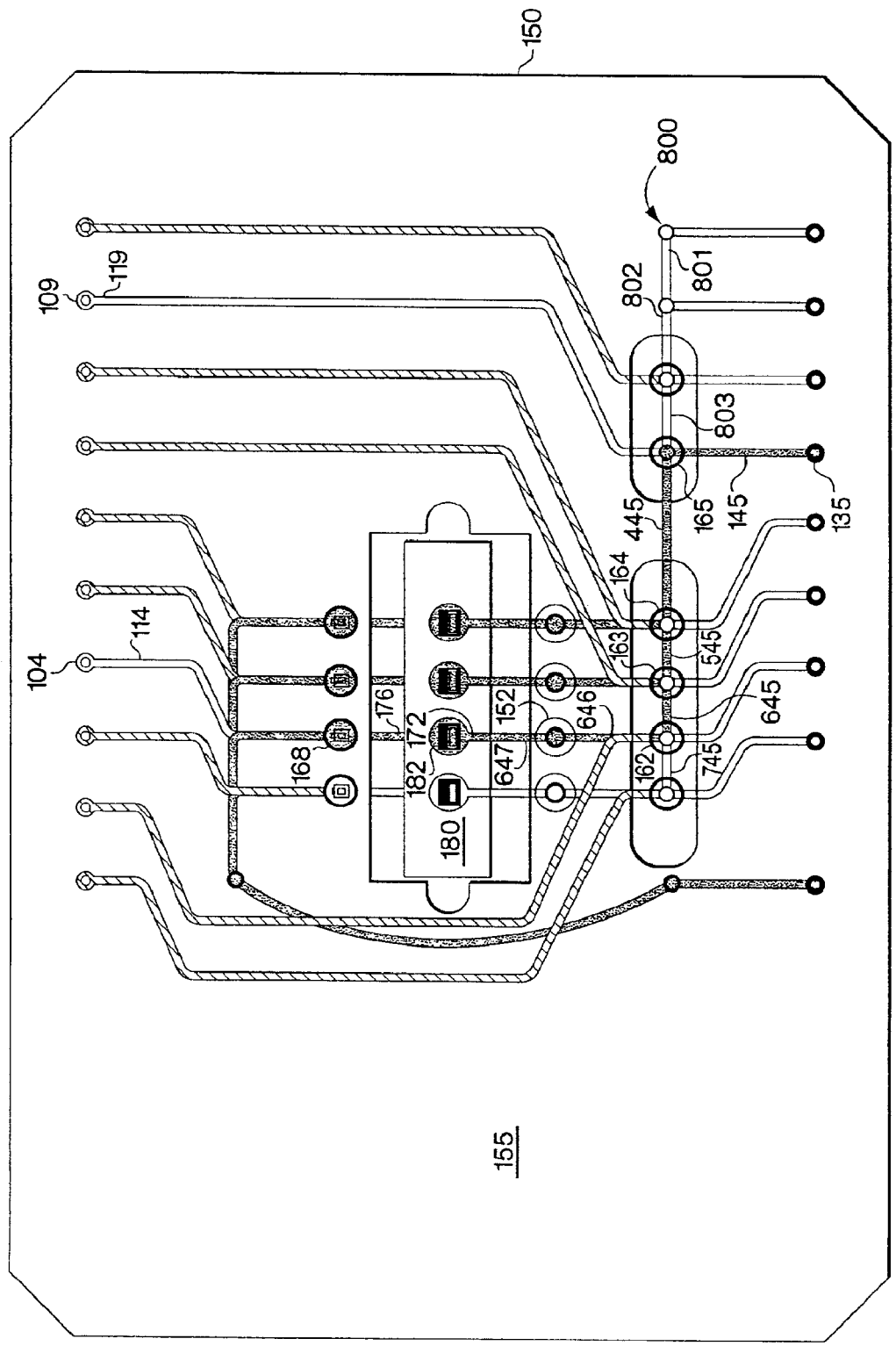
FIG. 6 is a graphical illustration of the embodiment of FIG. 1 showing a linker solution added to a third interaction cell.
Figure 7:
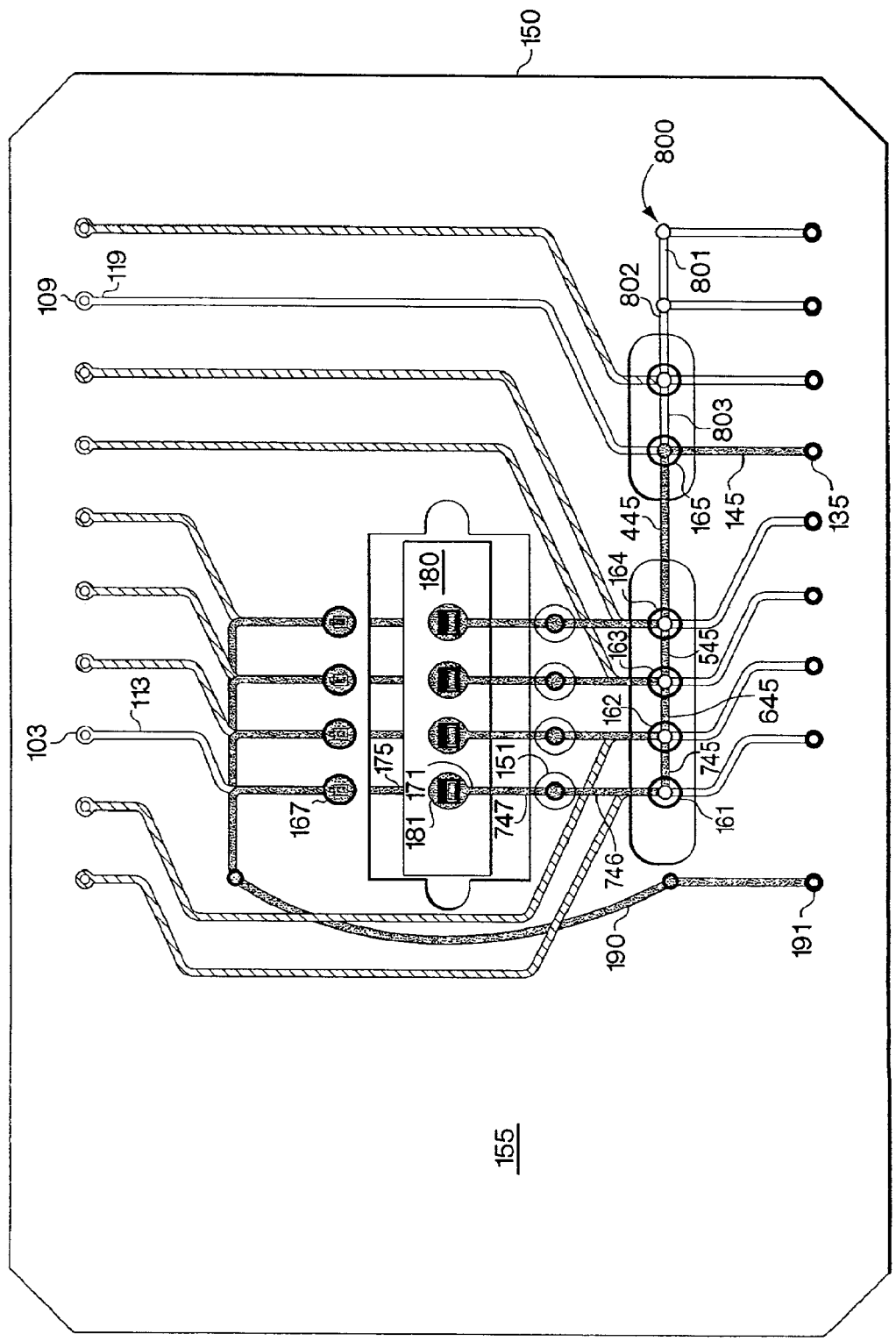
FIG. 7 is a graphical illustration of the embodiment of FIG. 1 showing a linker solution added to a fourth interaction cell.

FIGS. 6 and 7 show the linker solution being added to interaction cells 182 and 181 respectively. In accordance with this embodiment, each interaction cell 182 and 181 will receive the linker solution while all other cells are isolated in the manner described above with respect to FIGS. 4 and 5. To add the linker solution to interaction cell 182, control fluid will not be pressurized in control lines 114 and 119, causing valves 165 and 168 to open. Linker solution will flow from a fluid pump to inlet 135 into fluid line 145 and then through fluid paths 445, 545, and 645. The fluid will then flow into fluid path 646, and into expansion chamber 152. Gas will be eliminated from the linker solution in the expansion chamber 152, and the linker solution will flow through fluid path 647 into interaction cell 182 via inlet 172. Outflow of fluid from the interaction cell 182 will flow into output line 176, and because valve 168 is open, the outflow will be stored in a waste receptacle via fluid waste line 190 and waste outlet 191.

To add the linker solution to interaction cell 181, control fluid is not pressurized in control lines 113 and 119, causing valves 165 and 167 to open. Linker solution will flow from a fluid pump to inlet 135 into fluid line 145 and then through fluid paths 445, 545, 645, and 745. The fluid will then flow into fluid path 746, and into expansion chamber 151. Gas will be eliminated from the linker solution in the expansion chamber 151, and the linker solution will flow through fluid path 747 into interaction cell 181 via inlet 171. Outflow of fluid from the interaction cell 181 will flow into output line 175, and because valve 167 is open, the outflow will be stored in a waste receptacle via fluid waste line 190 and waste outlet 191.

The linker solution may be added to a subset of the plurality of interaction cells, or to all of the interaction cells, illustrated here for exemplary purposes only as four of the cells 181, 182, 183 and 184, by opening valve 165 with valves 167, 168, 169 and 170 simultaneously. Similarly, any subset of interaction cells may receive linker solution simultaneously by opening valve 165 and the valves that correspond to the interaction cells to be filled. Further, waste line 190 may lead to a plurality of reservoirs, and the outflow from the interaction cells may be stored in respective reservoirs for further analysis. Valves may be provided to insure that outflow from each interaction cell is stored in its corresponding reservoir. Alternatively, reservoir lines and outlets may be provided for each interaction cell, rather than one line and outlet (such as waste line 190 and outlet 191).

Figure 8:
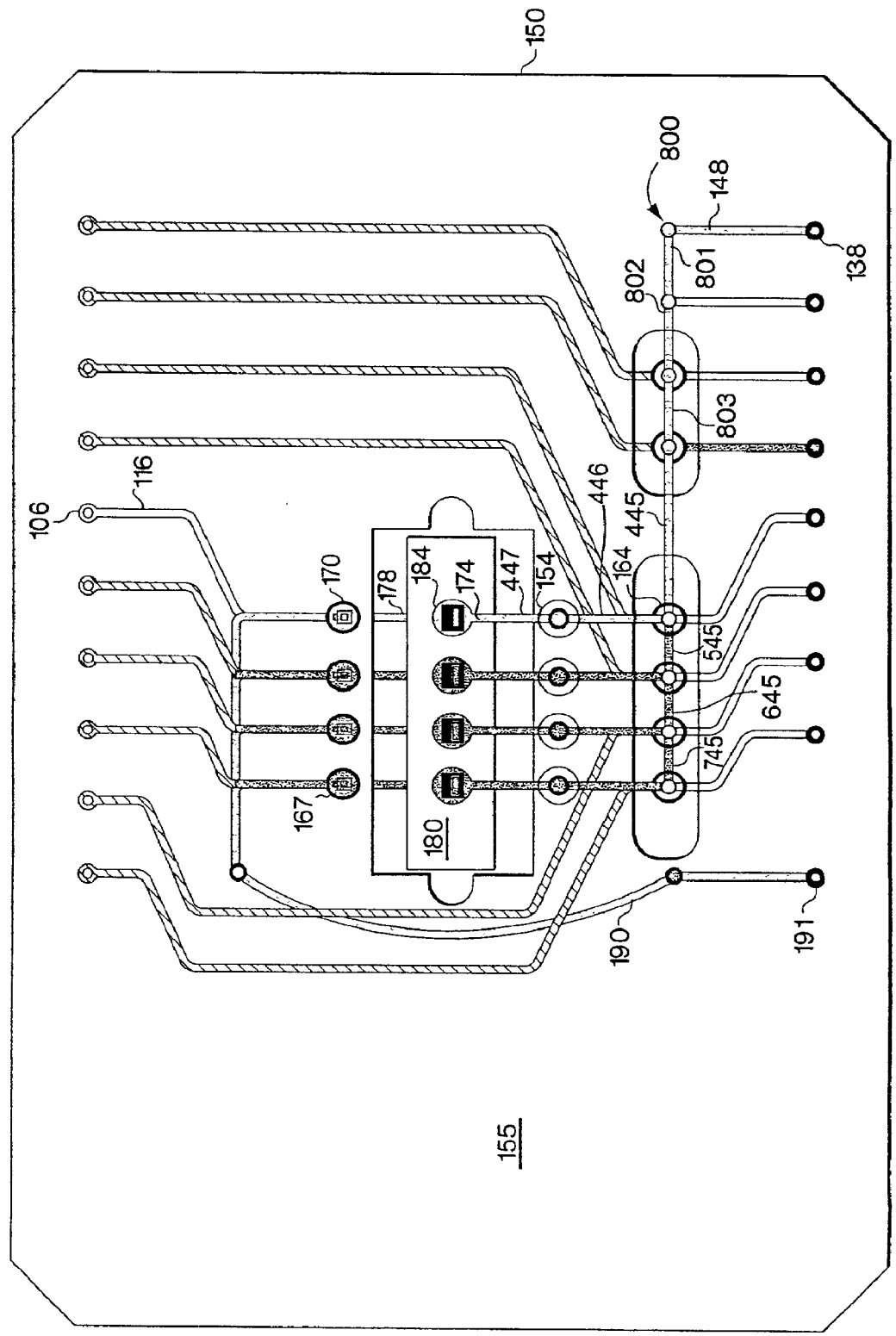
FIG. 8 is a graphical illustration of the embodiment of FIG. 1 showing a wash solution added to a first interaction cell.

FIG. 8 is a graphical illustration of the embodiment of FIG. 1 showing a wash solution added to a first interaction cell. The wash solution will flow from a fluid pump or other fluid delivery device to fluid line 148 via inlet 138. In accordance with this embodiment, no control line is in direct communication with fluid line 148 (though such a control line could be provided) thus, only control line 116 is de-pressurized. Valve 170 is opened, allowing the wash solution to flow into fluid path 445 via fluid paths 801–803. From this point, the wash process continues as described above with respect to the linker solution and FIGS. 4–7, to provide each interaction cell with the wash solution.

Figure 9:
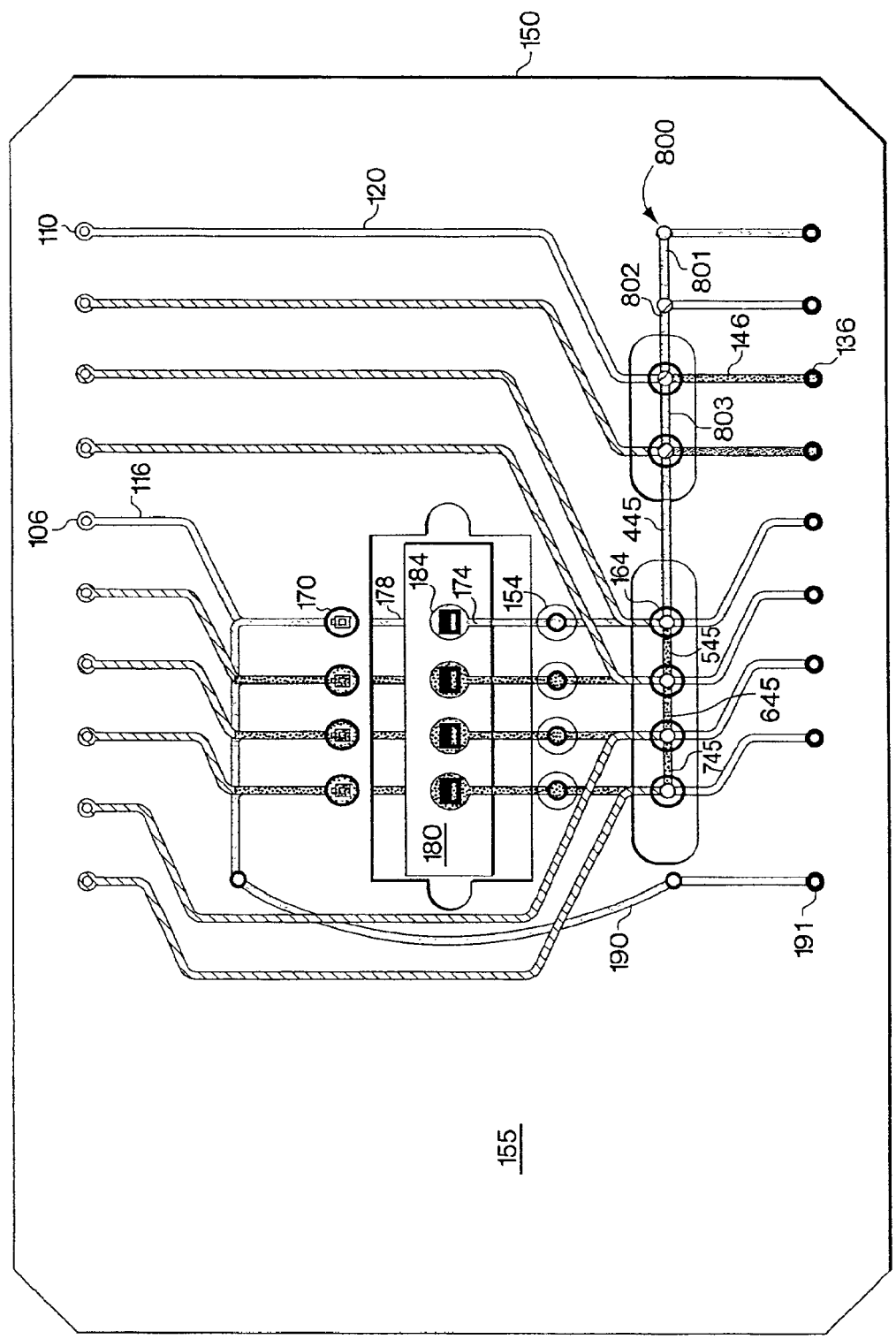
FIG. 9 is a graphical illustration of the embodiment of FIG. 1 showing a ligand solution added to a first interaction cell.

FIG. 9 is a graphical illustration of the embodiment of FIG. 1 showing a ligand solution, for example, an antibody solution, added to a first interaction cell. The ligand may react chemically with previously applied linker molecules. The ligand solution flows from a fluid pump or other fluid delivery device to fluid line 146 via inlet 136. Control lines 116 and 110 are de-pressurized and valves 170 and 166 are opened, allowing the ligand solution to flow into fluid path 445 via fluid path 803. From this point, the ligand solution proceeds through the apparatus as described above with respect to the linker and wash solutions to provide each interaction cell with the ligand solution.

Figure 10:
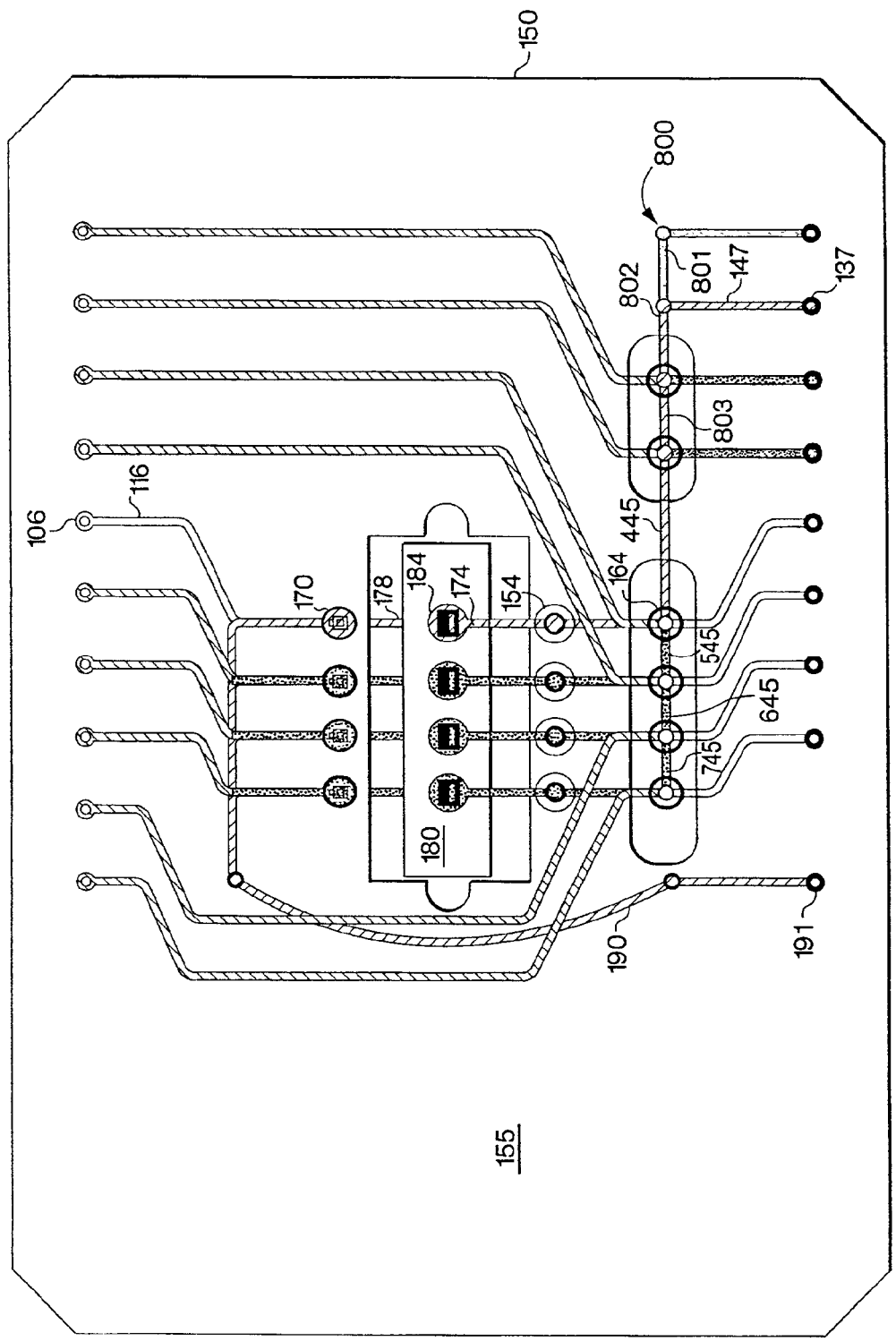
FIG. 10 is a graphical illustration of the embodiment of FIG. 1 showing a buffer solution added to a first interaction cell.

FIG. 10 is a graphical illustration of the embodiment of FIG. 1 showing a buffer solution added to a first interaction cell. The buffer solution flows from a fluid pump or other fluid delivery device to fluid line 147 via inlet 137. As was the case with the wash solution, no control line is in direct communication with fluid line 147 (again, such a control line could be provided), thus only control line 116 is de-pressurized. Valve 170 is opened, allowing the buffer solution to flow into fluid path 445 via fluid paths 802–803. From this point, the buffer solution proceeds to each interaction cell in accordance with the embodiments of FIGS. 4–7. A wash process may follow the addition of the buffer solution to each cell and will proceed as described above with respect to FIG. 8.

Figure 11:
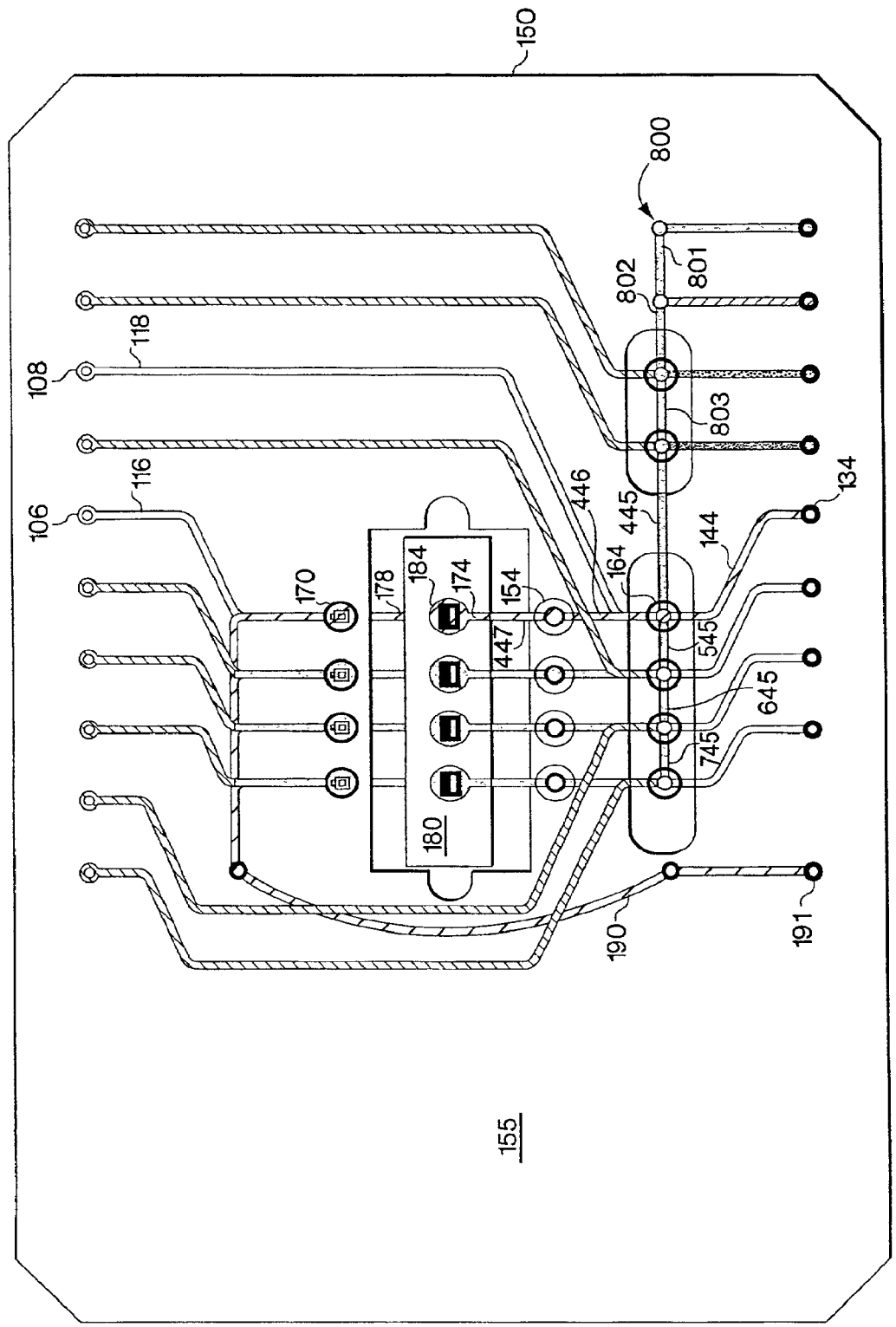
FIG. 11 is a graphical illustration of the embodiment of FIG. 1 showing a sample solution added to a first interaction cell.

In FIG. 11, a first sample solution having an analyte, or a control solution, is added to the first interaction cell. The first sample solution flows from a fluid pump or other fluid delivery device to fluid line 144 via inlet 134. Control lines 116 and 118 are de-pressurized and valves 170 and 164 are opened, allowing the first sample solution to flow into fluid path 446 and into expansion chamber 154. From this point, the first sample solution proceeds to the interaction cell 184 via fluid path 447 and inlet 174. Outflow of the first sample solution from the interaction cell 184 will flow into output line 178, and the outflow will be stored in a waste receptacle (or reservoir for collection) via waste line 190 (or reservoir line) and waste outlet (or reservoir outlet) 191.

Figure 12:
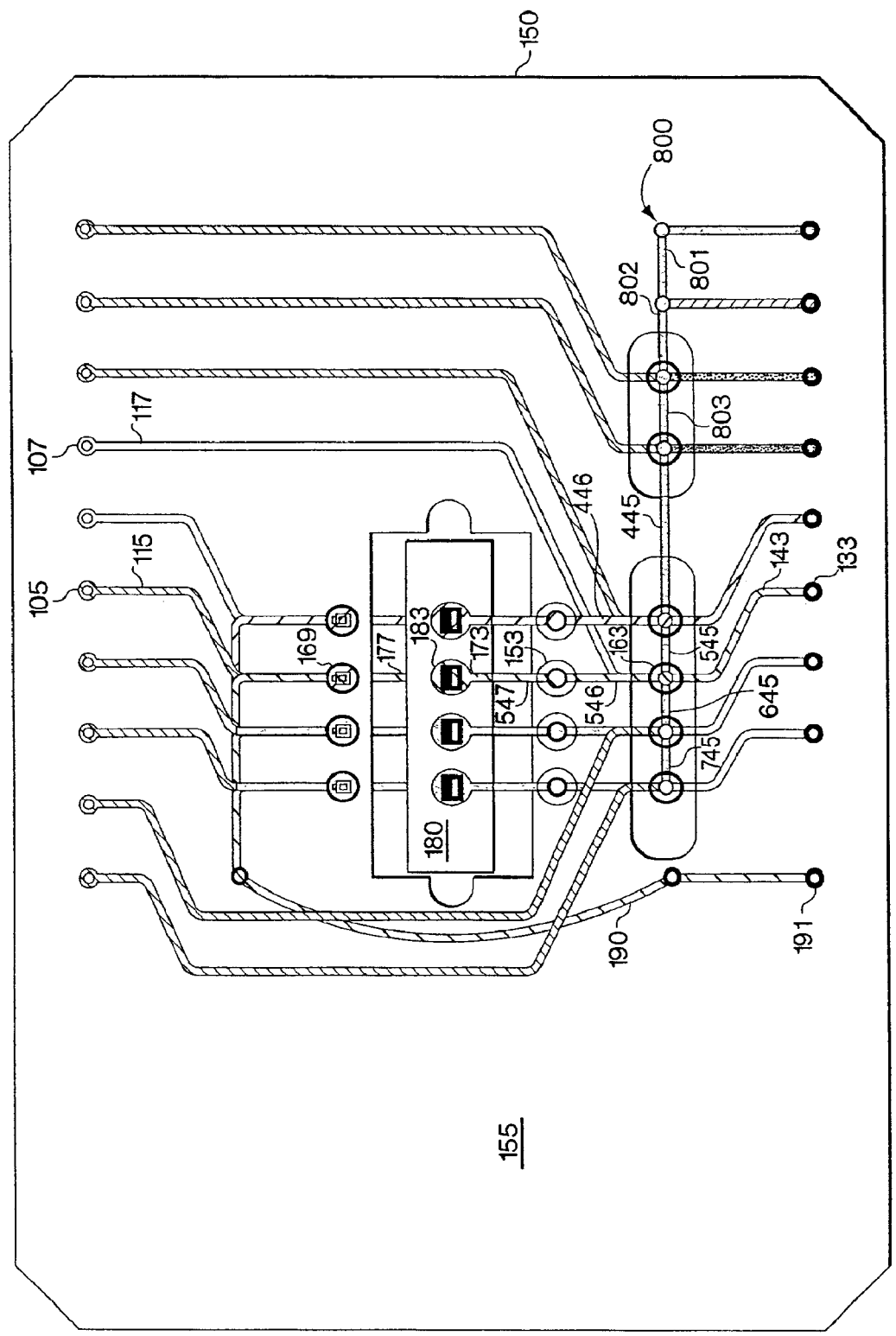
FIG. 12 is a graphical illustration of the embodiment of FIG. 1 showing a sample solution added to a second interaction cell.

FIG. 12 is a graphical illustration showing that the second interaction cell may be provided with a second sample solution. To provide interaction cell 183 with the second sample solution, control lines 115 and 117 are de-pressurized, valves 169 and 163 are opened and the second sample solution flows from a fluid pump to fluid line 143 via inlet 133. The second sample solution will flow into fluid path 546 and into expansion chamber 153. The second sample solution proceeds to the interaction cell 183 via fluid path 547 and inlet 173. As above, outflow of the second sample solution from the interaction cell 183 will flow into output line 177, and the outflow will be stored in a waste receptacle (or reservoir for collection) via waste line 190 and waste outlet 191.

Figure 13:
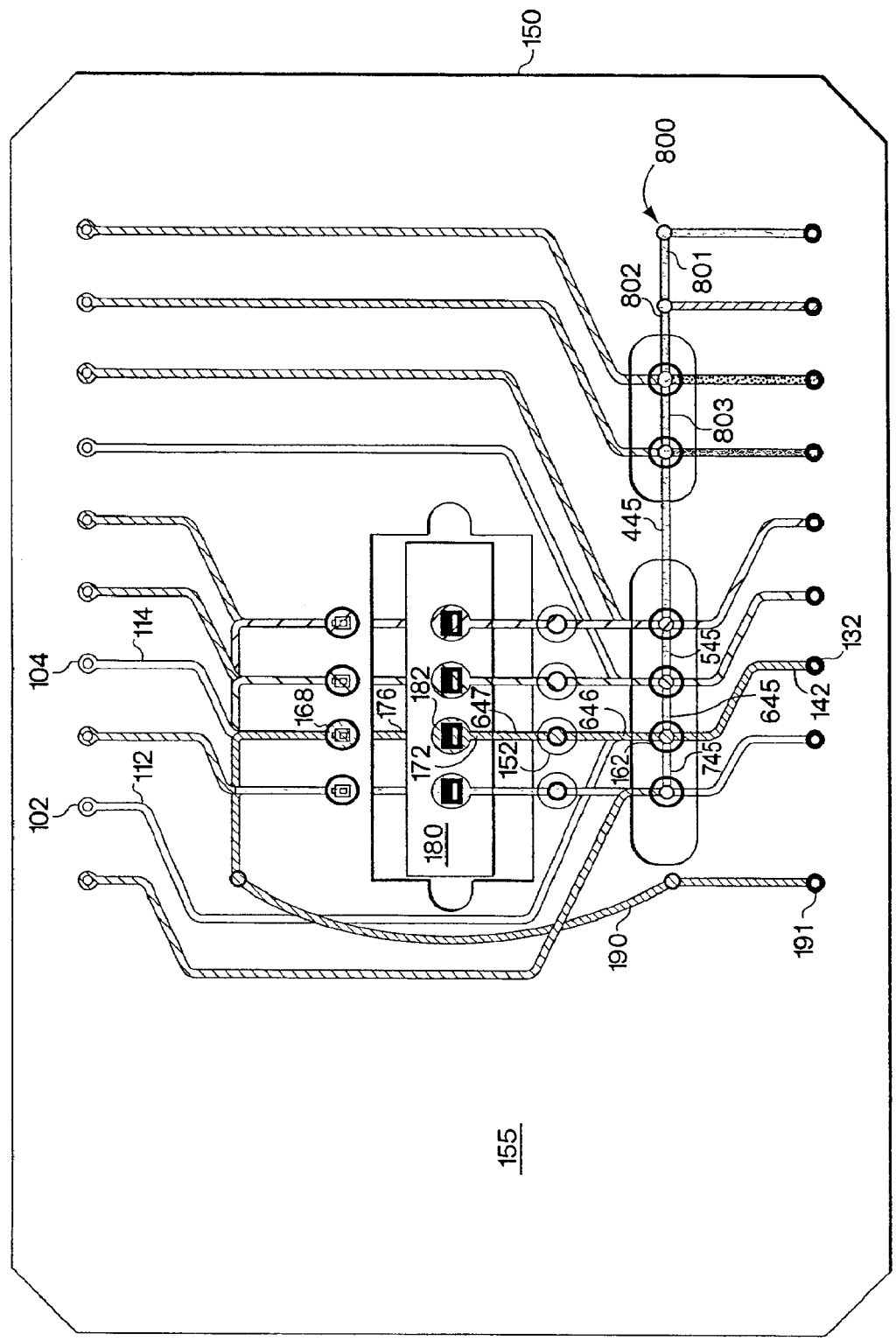
FIG. 13 is a graphical illustration of the embodiment of FIG. 1 showing a sample solution added to a third interaction cell.

FIG. 13 illustrates a way to provide the third interaction cell 182 with a third sample solution, control lines 112 and 114 are de-pressurized, valves 162 and 166 are opened and the third sample solution flows from a fluid pump to fluid line 142 via inlet 132. The third sample solution will flow into fluid path 646 and into expansion chamber 152 and gas will be removed from the solution. The third sample solution proceeds to the interaction cell 182 via fluid path 647 and inlet 172. Outflow of the third sample solution from the interaction cell 182 will flow into output line 176, and the outflow will be stored in a waste receptacle (or reservoir for collection) via waste line 190 and waste outlet 191.

Figure 14:
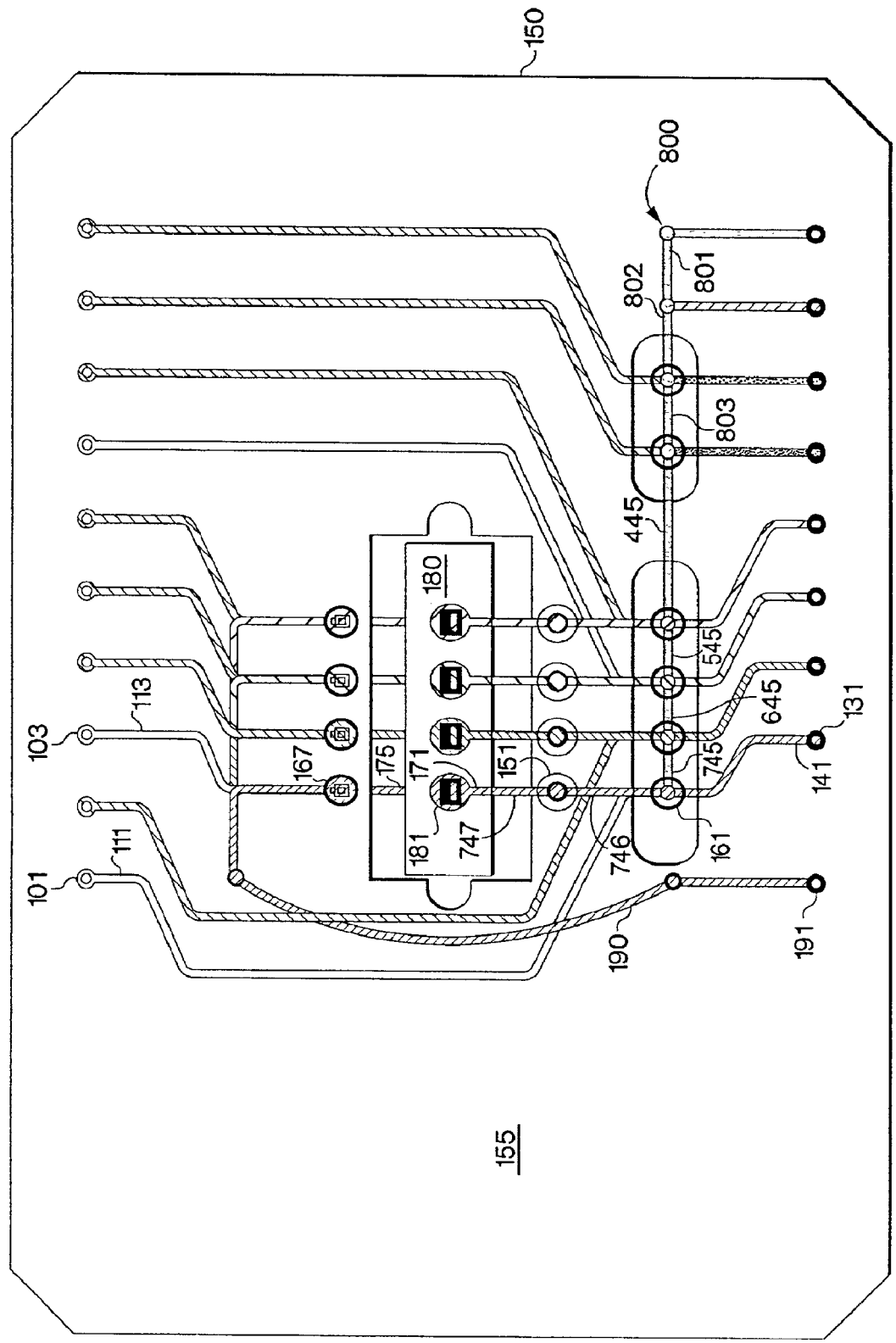
FIG. 14 is a graphical illustration of the embodiment of FIG. 1 showing a sample solution added to a fourth interaction cell.

FIG. 14 illustrates a way to provide the fourth interaction cell 181 with a fourth sample solution. Here, control lines 111 and 113 are de-pressurized, valves 161 and 167 are opened and the fourth sample solution flows from a fluid pump to fluid line 141 via inlet 131. The fourth sample solution will flow into path 746 and into expansion chamber 151, and gas will be removed from the solution. The fourth sample solution proceeds to the interaction cell 181 via fluid path 747 and inlet 171. Outflow of the fourth sample solution from the interaction cell 181 will flow into output line 175, and the outflow will be stored in a waste receptacle (or reservoir for collection) via waste line 190 and waste outlet 191.

Each of the interaction cells includes at least one microcantilever, or an array of microcantilevers, configured to deflect in response to chemical interactions with a component of the sample fluid. In a particular embodiment of the invention, a planar array of microcantilever fingers is disposed in each interaction cell such that one or more microcantilever finger deflects with respect to the plane of the array in response to a reaction with a molecular component of the sample solution.

Figure 15:
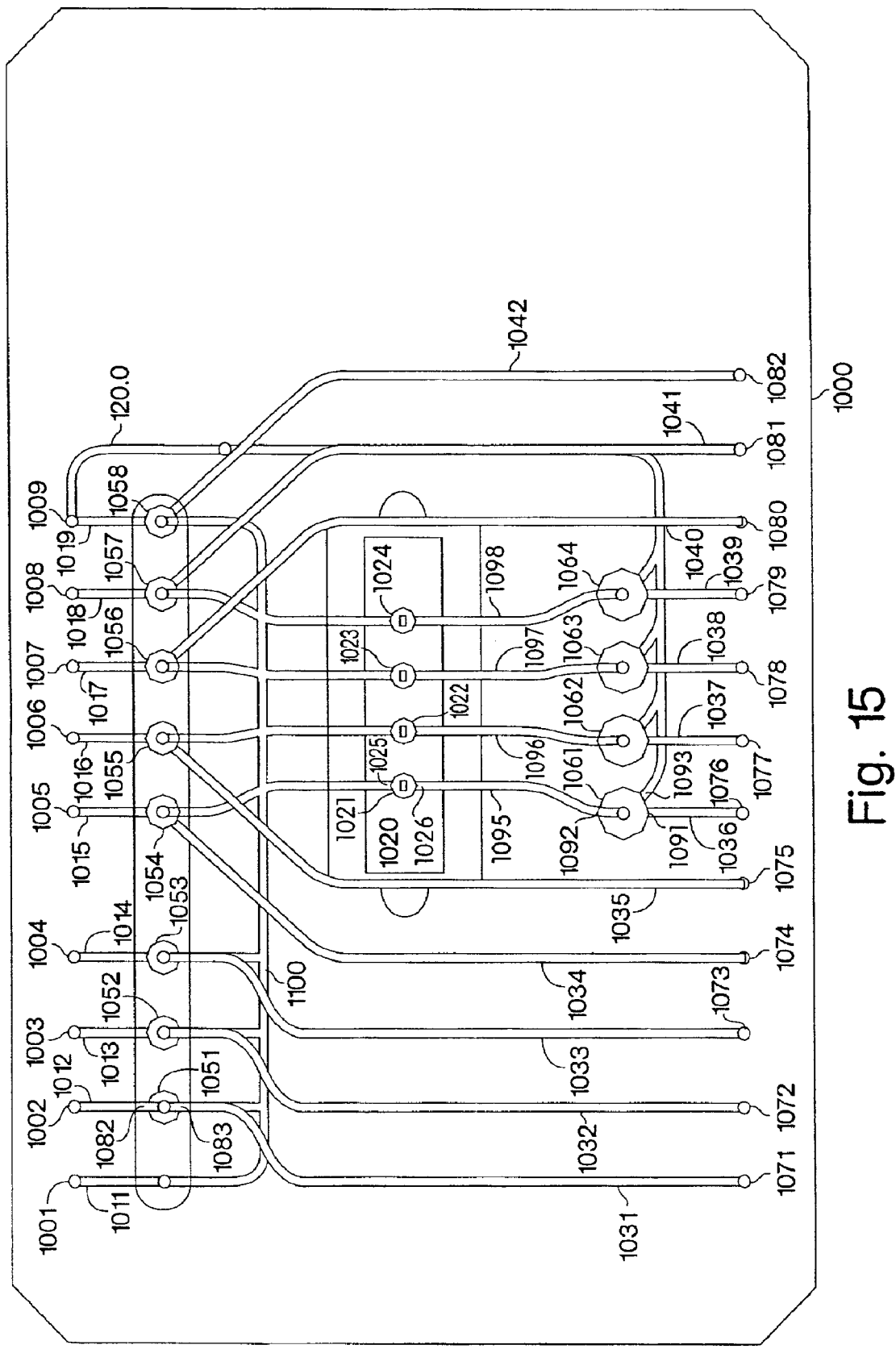
FIG. 15 is a graphical illustration of an apparatus for performing microfluidic analysis in accordance with another embodiment of the invention.

FIG. 15 is a graphical illustration showing an apparatus for performing microfluidic analysis in which the valves of the apparatus are normally closed in accordance with another embodiment of the invention. Unlike the embodiment of FIG. 1, in FIG. 15, all of the valves 1051–1058 and 1061–1064 are closed under normal atmospheric pressure. This configuration reduces the duty cycle of the electrical components of the system and minimizes the amount of current needed to drive the system. However, whether the valves are open or closed under normal atmospheric conditions is purely arbitrary and each of the embodiments of FIG. 1 and FIG. 15 may operate either way with respect to the configuration of lines and valves. Additionally, in accordance with the embodiment of FIG. 15, the fluid lines 1011–1019 and fluid inlets 1001–1008 are at the top of the figure, rather than at the bottom as in FIG. 1.

The apparatus includes a three-dimensional housing 1000 having a plurality of fluid lines 1011–1019. Each of the fluid lines 1011–1018 has an inlet 1001–1008 for receiving a fluid from a fluid pump or other fluid delivery apparatus. The housing 1000 also includes a plurality of control lines 1031–1042 in communication with the fluid lines 1011–1019. Each of the control lines 1031–1042 receives a control fluid from an inlet 1071–1082. The fluid lines 1011–1019, control lines 1031–1042 and fluid paths of this embodiment may be dimensioned in a manner similar to the fluid lines, control lines, and fluid paths described with respect to FIG. 1. Here again, control fluid and other fluids may be provided to the apparatus through the use of a robotic device, or may be provided manually.

The plurality of valves 1051–1058 and 1061–1064 control the flow of fluid into and out of a microcantilever platform 1020. The valves may be two-way valves that function as three-way valves as described above with respect to the embodiment of FIG. 1. Thus, each valve has an inlet and an outlet. For example, valve 1051 has a valve inlet 1082 for receiving the control fluid from control line 1031, a valve outlet 1083 for transmitting fluid from fluid line 1012 to the manifold 1100. The valves 1051–1058 and 1061–1064 are activated (in this case opened) by the control fluid. As above, when the control fluid is a high density gas the response time of the valves quickens. The valves may be activated or deactivated under control of a computer program resident on a microprocessor. Further, the number valves in the apparatus may be less than, more than or equal to the number of fluid lines. Similarly, the number of valves may be less than, equal to or more than the number of control lines.

The microcantilever platform 1020 is disposed in the housing 1000 and includes a plurality of interaction cells 1021–1024. Each of the interaction cells 1021–1024 has an inlet, such as 1025, for receiving one or more preparation fluids and a sample fluid and an outlet, such as 1026, for releasing fluid from the cell through output lines 1095–1098.

The apparatus of FIG. 15 may further include a waste line 1200 with a waste outlet 1009 for releasing waste from the interaction cells 1021–1024 into a waste receptacle. As was the case with the embodiment of FIG. 1, each interaction cell 1021–1024 may be in fluid communication with its own waste receptacle or with a reservoir for collecting the contents of the interaction cell in order to perform further analysis on what is contained in the reservoir.

As was the case with the apparatus of FIG. 1, the embodiment of FIG. 15 may be in the form of a card or cartridge comprising one more plastic polymers. Preparation fluids, such as linker, buffer, ligand solutions, and sample solutions may be input to the interaction cells 1021–1024 in a discriminatory manner. A buffer solution may be input to all of the cells or to a subset of the cells, for example, to three of the cells, two of the cells or only to one of the cells. Similarly, a different sample solution may be input to each of the cells, or to a subset of the cells.

Figure 16:
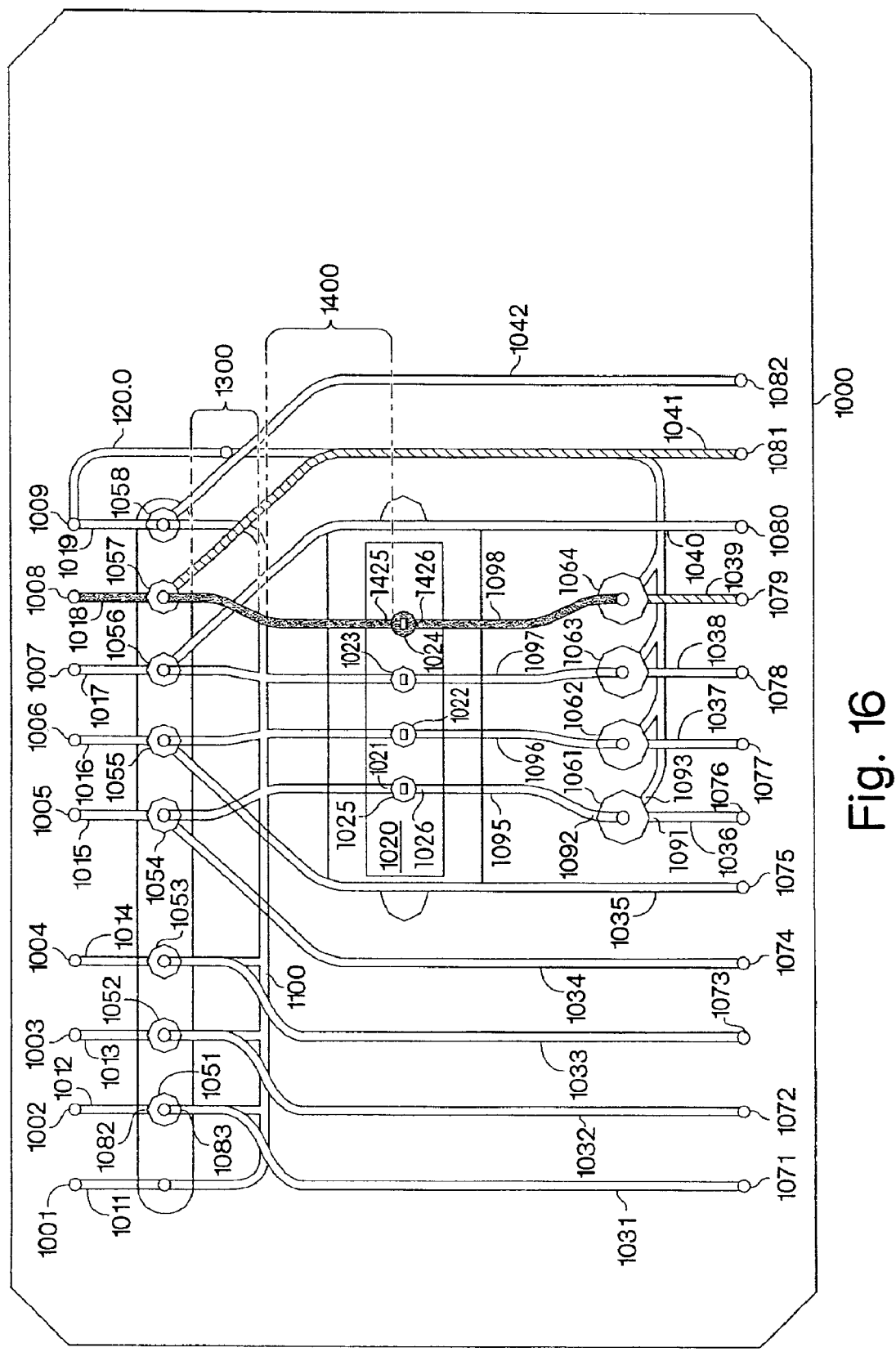
FIG. 16 is a graphical illustration of the embodiment of FIG. 15 showing a solution added to a first interaction cell.

FIG. 16 shows a solution being added to a first interaction cell. To accomplish this, inlets 1081 and 1079 receive the control gas, thus control gas is input to control lines 1041 and 1039 respectively, and valves 1057 and 1064 are opened. The solution flows from a fluid pump or other fluid delivery device to inlet 1008 into fluid line 1018. Since valve 1057 is open, the fluid may then flow through fluid path 1300 into fluid path 1400, and into interaction cell 1024 via inlet 1425. Any outflow of fluid from the interaction cell 1024 will flow into output line 1098, and because valve 1064 is open, the outflow will be stored in a waste receptacle (or in a reservoir for collection) via fluid waste line 1200 and waste outlet 1009.

The solution may be added to a subset of the plurality of interaction cells, or to all of the interaction cells, illustrated here for exemplary purposes only as four cells. Similarly, any subset of interaction cells may receive a solution simultaneously by opening the valves that correspond to the appropriate interaction cells to be filled (as will be evident from the descriptions FIGS. 16–20). Further, the waste line 1200 may lead to a plurality of reservoirs, and the outflow from the interaction cells may be stored in respective reservoirs for further analysis. Valves may be provided to insure that outflow from each interaction cell is stored in its corresponding reservoir. Alternatively, reservoir lines and outlets may be provided for each interaction cell, rather than one line and outlet.

Figure 17:
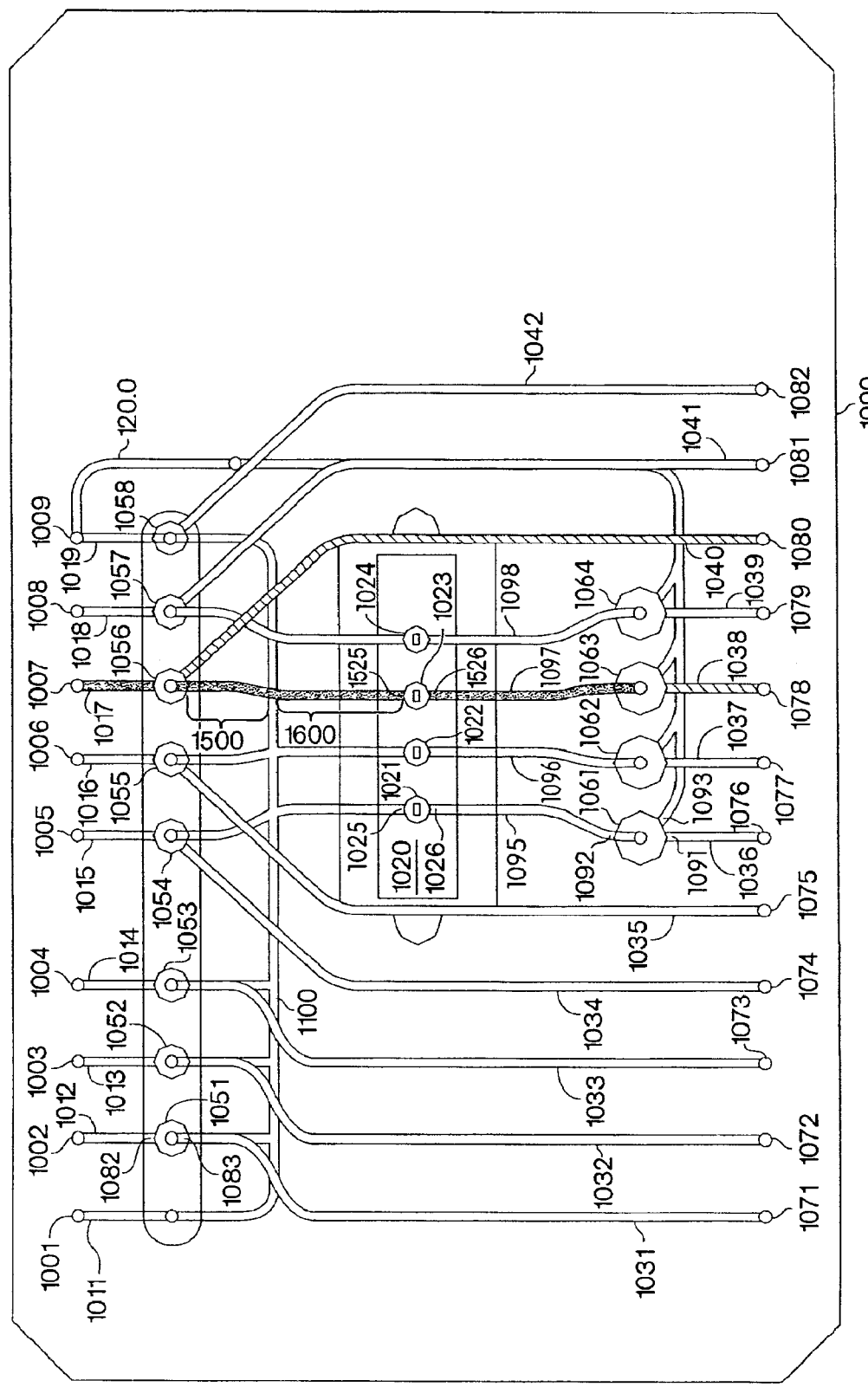
FIG. 17 is a graphical illustration of the embodiment of FIG. 15 showing a solution added to a second interaction cell.

FIG. 17 is a graphical illustration of the embodiment of FIG. 15 showing a solution added to a second interaction cell. Here, inlets 1080 and 1078 receive the control gas, thus control gas is input to control lines 1040 and 1038 respectively, and valves 1056 and 1063 are opened. The solution flows to inlet 1007 into fluid line 1017. Since valve 1056 is open, the fluid may then flow through fluid path 1500 into fluid path 1600, and into interaction cell 1023 via inlet 1525. Any outflow of fluid from the interaction cell 1023 will flow into output line 1097, and because valve 1063 is open, the outflow will be stored in a waste receptacle or reservoir via fluid waste line 1200 and waste outlet 1009.

Figure 18:
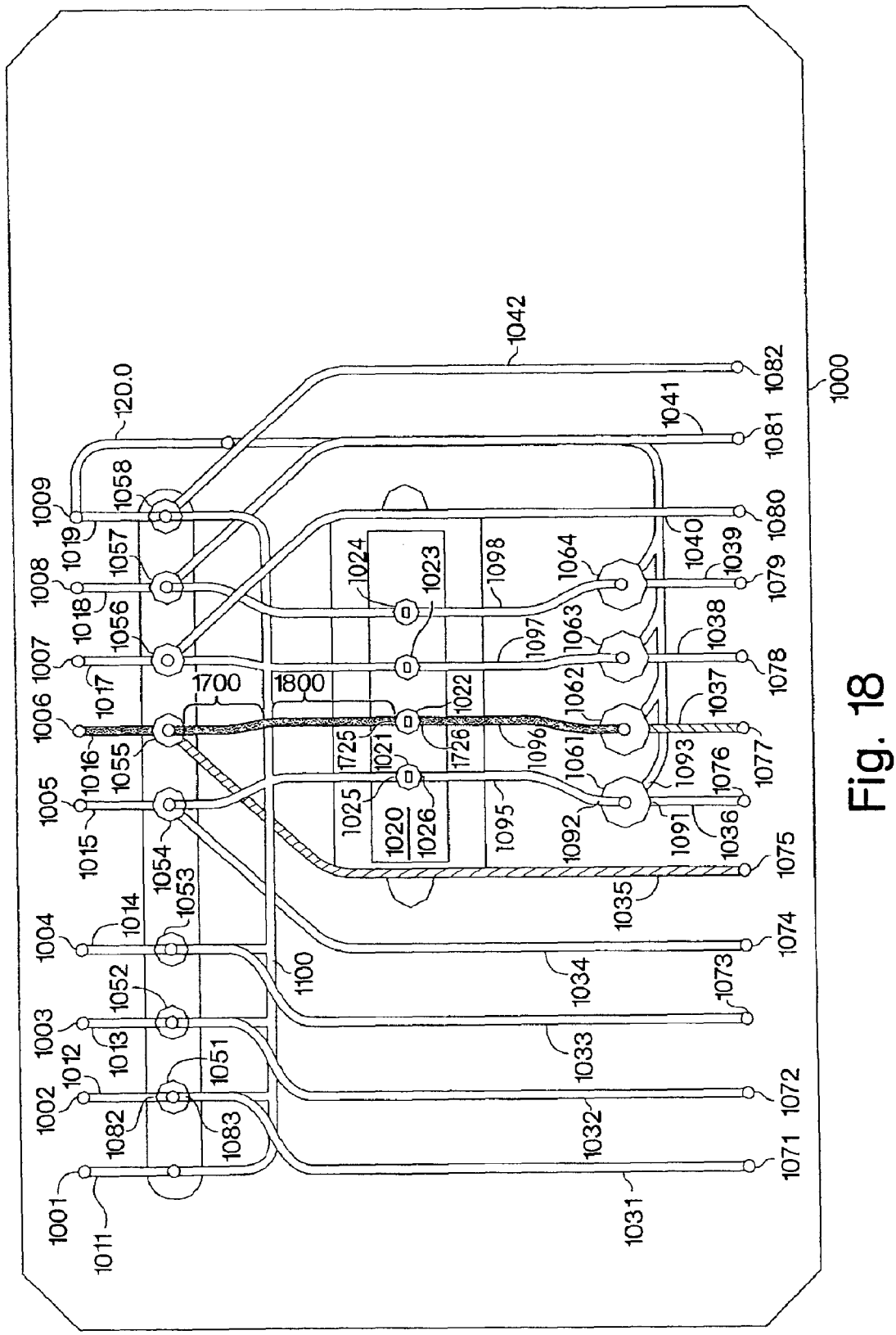
FIG. 18 is a graphical illustration of the embodiment of FIG. 15 showing a solution added to a third interaction cell.

FIG. 18 is a graphical illustration of the embodiment of FIG. 15 showing a solution added to a third interaction cell. Inlets 1075 and 1077 receive the control gas, and control gas is input to control lines 1035 and 1037 respectively. Valves 1055 and 1062 are opened. The solution flows from a fluid pump or other fluid delivery device to inlet 1006 into fluid line 1016. Since valve 1055 is open, the fluid may then flow through fluid path 1700 into fluid path 1800, and into interaction cell 1022 via inlet 1725. Again, outflow of fluid from the interaction cell 1022 will flow into output line 1096, and because valve 1062 is open, the outflow will be stored via fluid waste line 1200 and waste outlet 1009.

Figure 19:
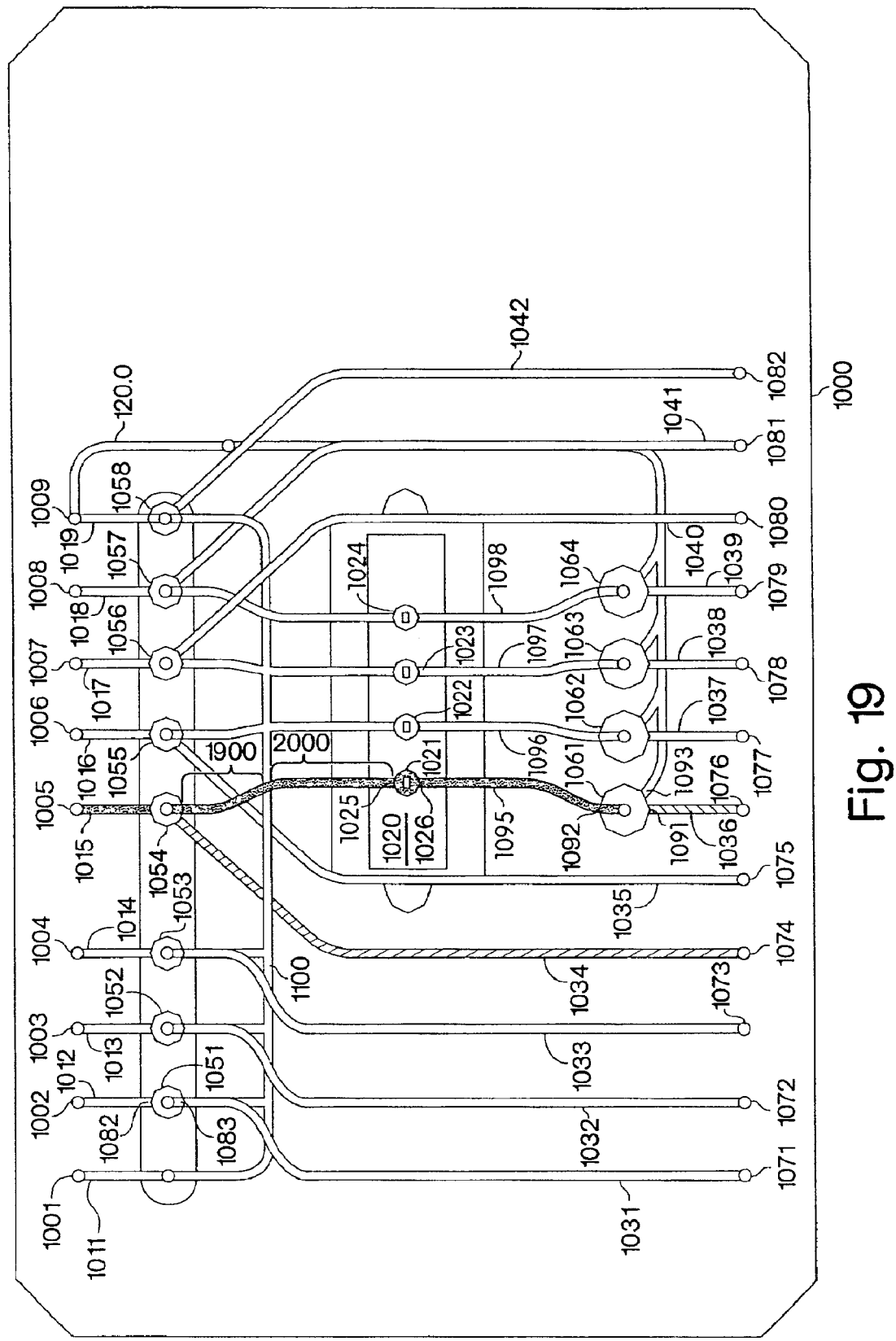
FIG. 19 is a graphical illustration of the embodiment of FIG. 15 showing a solution added to a fourth interaction cell.

FIG. 19 is a graphical illustration of the embodiment of FIG. 15 showing a solution added to a fourth interaction cell. Inlets 1074 and 1076 receive the control gas, which is input to control lines 1034 and 1036 respectively. Valves 1054 and 1061 are opened, and the solution flows from to inlet 1005 into fluid line 1015. Since valve 1054 is open, the fluid may then flow through fluid path 1900 into fluid path 2000, and into interaction cell 1021 via inlet 1225. Any outflow of fluid from the interaction cell 1021 will flow into output line 1095, and because valve 1061 is open, the outflow will be stored in a waste receptacle or reservoir via fluid waste line 1200 and waste outlet 1009.

FIG. 20 is a schematic flow chart illustrating fluidics system for use in accordance with a method for identifying an analyte in a plurality of sample fluids in accordance with a further embodiment of the invention. In accordance with this embodiment, one or more preparation solutions 901–904 are input into one or more of a plurality of interaction cells. At least one of the preparation fluids includes a ligand that has affinity for the analyte. Each interaction cell includes at least one microcantilever such that the ligand binds to the microcantilever. At least one sample solution 905–908 is input into one or more of the interaction cells, and a deflection of the microcantilever in is detected in each sample solution containing the analyte. In one embodiment, the device may be mounted in a manifold and/or on a temperature-controlled platform. Outflow from the interaction cells 910–913 may be stored in a waste receptacle 909 or in a reservoir for further analysis as described above.

One of the preparation fluids may be a solution of a linker 901 capable of covalently linking the ligand, here defined as the material affixed to a surface of the microcantilever, to the microcantilever. Another preparation fluid may be a wash solution 902, and the wash solution may be input to one or a plurality of the interaction cells one or more times. Yet another preparation fluid may be a ligand or a "receptor" solution 903, i.e., a biological macromolecule known to have affinity for a specific binding portion, or a ligand for a class of analytes. The receptor can also be a ligand for an analyte, the presence and/or amount of which is to be detected in one or in a series of sample. Another preparation fluid may be a buffer solution 904. The number of sample solutions may equal the number of interaction cells or the number of sample solutions may be less than the number of interaction cells.

The ligand may be a biomaterial, for example, a protein such as an enzyme or a synthetic polypeptide, or it can be a nucleic acid such as RNA or DNA. A biomaterial that is a macromolecule may comprise all or a portion of a nucleic acid or a protein. The protein or polypeptide may comprise an epitope, an antibody, an antibody fragment, an enzyme, or any other embodiment of a molecule containing peptide bonds. The analyte to be detected or quantified in a sample may be a biomaterial such as a macromolecule, or an organic or inorganic small molecule. Similarly, the analyte may be hormone, for example, the hormone may be a steroid for example, a sex steroid or a glucocorticoid, or a polypeptide hormone such as a cytokine. Either of the ligand or the analyte may comprise all or a portion of an antibody or an antigenic material, or all or a portion of an enzyme.

Examples and methods for the use of the apparatus of the invention are shown in Table 1. In Example 1, the apparatuses of FIGS. 3–19 is used to demonstrate a movement or deflection of a plurality of microcantilevers in a microcantilever array when a sample solution contains an analyte, such as a particular chemical or biological component, capable of binding to or interacting with a ligand affixed to a surface of the microcantilever. Cell A can be a reaction cell that provides a positive control; deflection of microcantilevers is caused by interaction on a surface of the cantilever of components of fluids sequentially provided to cell A. Cell B can be a reference cell; for example, a control buffer known to lack the analyte, is added to this cell instead of a sample. This control can determine the extent of microcantilever deflection that occurs as a result of interactions between preparation liquids such as a linker solution and an antibody solution, or other environmental forces. Cell C can be a negative control cell, for example, which has not been exposed to linker solution. Microcantilever deflection in this cell can determine the extent of ligand binding to a microcantilever surface density, in the absence of a cross-linking agent. Cell D can be another control cell, containing for example, bovine serum albumin instead of the biomaterial of interest, so that microcantilever deflection is a measure of non-specific binding of the analyte.

The contents of all cited references are hereby incorporated by reference herein.

EXAMPLE 1

In accordance with step 1 of Example 1 as illustrated in Table 1, the cross-linking agent DSU (dithiobis (succinimidylundecanoate)) in a volume of about 50 μl, is added to interaction cells A, B and D. DSU is a water soluble bifunctional cross-linking agent.

In step 2, as herein exemplified, all of the cells receive a wash solution in a volume of about 300 μl per cell. In step 3, all of the cells can receive about 50 μl of an antibody solution (such as an antibody specific for an oncogene protein such as Brc A or Wilm's Tumor, WT-1). A buffer having a low pH is provided to interaction cells, for example, to cells A, B and D, in a volume of about 50 μl per cell in step 4. This solution removes non-specifically bound material, i.e., those molecules of material which have not reacted with the cross-linking agent. Cells are washed with about 300 μl of the wash solution in step 5. In step 6, a volume of a sample solution containing, for example, an unknown quantity of a material that can interact with the antibody of step 3, for example, about 50 μl is provided to cells, for example, to cells A and C. A control material, e.g., bovine serum albumin is provided to cell D in a volume of about 50 μl in step 7. Cells are washed, for example, with about 300 μl of the wash solution in step 8.

Further in Example 1, it should be noted that the wash steps can be performed with the same solution, and that steps, for example, steps 6 and 7, can be preformed simultaneously. Further, any of the wash steps are optional in to volume and timing; deflection of microcantilevers can be analyzed throughout, although measurement of deflection following steps 6 and 7 is most significant.

It is to be understood that a choice of a volume of fluid to use is merely suggested here and can be varied from the suggested amounts. Volumes for other use in the methods and apparatuses herein can be standardized within any given experiment according to a protocol to be devised by a user of ordinary skill in the art, and such alternative volumes are within the equivalents envisioned herein.

EXAMPLE 2

Example 2 is an illustration of how the apparatus described herein may be used to identify a ligand in a plurality of sample solutions. Here cells A, B and C are reaction cells and cell D is used as a control cell. A volume, for example, of about 50 μl of DSU is provided to each cell in step 1. Next in step 2, a wash solution is provided to each cell in a volume of, for example, about 300 μl per cell. In steps 3 and 4, each cell is provided with about 50 μl of antibody solution and buffer solution respectively, and in step 5 the cells are subjected to another wash. A first sample solution, in a volume of about 50 μl, is then added to cell A in step 6. A second sample solution, also in volume of about 50 μl, is added to cell B in step 7, and a third sample solution of the same volume is added to cell C in step 8. It should be noted that in accordance with the apparatus described above, the first, second and third sample solutions may be provided to cells A, B and C, respectively, in one step. All of the cells are subjected to an optional wash process in step 9. Further, the solutions in one or more of the cells may be reused. That is, additional solutions may be added to one or more of the cells for further analysis.

EXAMPLE 3

Example 3 illustrates how the apparatus described herein may be used to diagnose a patient simultaneously for one of a plurality of different viruses. Cells A, B and C are reaction cells and cell D is used as a control cell. A volume, for example, of about 50 μl of DSU is provided to each cell in step 1. In step 2, a wash solution is provided to each cell in a volume of, for example, about 300 μl per cell. In step 3 cell A is provided with about 50 μl of a first antibody solution. In step 4 cell B is provided with about 50 μl of a second antibody solution, and in step 5 cell C is provided with about 50 μl of a third antibody solution. Each antibody solution can have binding determinants directed against one of the viruses for the diagnosis. A volume of about 50 μl, of buffer solution is added to each of the cells step 6. All of the cells are then provided with about 300 μl of a wash solution in step 7, and in step 8 a volume of about 50 μl of a first, second, third sample solutions is provided to cells A, B, and C. The first, second and third antibody solutions may be provided to cells A, B and C, respectively, in one step. All of the cells can be subjected to an optional wash process in step 9.

Although various exemplary embodiments of the invention have been disclosed, it should be apparent to those skilled in the art that various changes and modifications can be made which will achieve some of the advantages of the invention without departing from the true scope of the invention.

TABLE I

Example 1

| Step | Solution | Total Vol μl (All Cells) | A Reaction | B Ref | C NSB | D BSA |
|---|---|---|---|---|---|---|
| 1 | DSU | 50 | + | + | 0 | + |
| 2 | Wash | 300 | + | + | + | + |
| 3 | Ab | 50 | + | + | + | + |
| 4 | Hbuffer | 50 | + | + | 0 | + |
| 5 | Wash | 300 | + | + | + | + |
| 6 | Sample | 50 | + | 0 | + | 0 |
| 7 | BSA | 50 | 0 | 0 | 0 | + |
| 8 | Wash | 300 | + | + | + | + |

Example 2

| Step | Solution | Total Vol μl (All Cells) | A Reaction | B Reaction | C Reaction | D Control |
|---|---|---|---|---|---|---|
| 1 | DSU | 50 | + | + | + | + |
| 2 | Wash | 300 | + | + | + | + |
| 3 | Ab | 50 | + | + | + | + |
| 4 | Hbuffer | 50 | + | + | + | + |
| 5 | Wash | 300 | + | + | + | + |
| 6 | Sample 1 | 50 | + | 0 | 0 | 0 |
| 7 | Sample 2 | 50 | 0 | + | 0 | 0 |
| 8 | Sample 3 | 50 | 0 | 0 | + | 0 |
| 9 | Wash | 300 | + | + | + | + |

Example 3

| Step | Solution | Total Vol μl (All Cells) | A Reaction | B Reaction | C Reaction | D Control |
|---|---|---|---|---|---|---|
| 1 | DSU | 50 | + | + | + | + |
| 2 | Wash | 300 | + | + | + | + |
| 3 | Ab 1 | 50 | + | 0 | 0 | 0 |
| 4 | Ab 2 | 50 | 0 | + | 0 | 0 |
| 5 | Ab 3 | 50 | 0 | 0 | + | 0 |
| 6 | Hbuffer | 50 | + | + | + | + |
| 7 | Wash | 300 | + | + | + | + |
| 8 | Sample | 50 | + | + | + | 0 |
| 9 | Wash | 300 | + | + | + | + |

What is claimed is:

1. A microfluidic device for analyzing a plurality of sample fluids, the device comprising:
   a plurality of interaction cells;
   a fluid control means including i) means for providing to the interaction cells a preparation fluid, and ii) means for providing to the interaction cells a sample fluid, wherein each interaction cell receives a different sample fluid, wherein the interaction cells and the fluid control means are within a housing; and
   a plurality of identically configured microcantilevers disposed in each of the interaction cells, wherein each of the plurality of microcantilevers within an interaction cell is identically configured to deflect in response to an interaction involving the same component of the sample fluid provided to the interaction cell, thereby analyzing the pluarality of sample fluids in the plurality of interaction cells.

2. A microfluidics device according to claim 1, wherein the fluid control means includes means for removing a fluid from the interaction cells.

3. A microfluidics device according to claim 1, wherein the fluid control means comprises a microprocessor with an integrated circuit containing control circuitry to control activation of the valves.

4. A microfluidics device according to claim 1, wherein the fluid control means comprises valves that lead to a common line or manifold comprising fluid paths.

5. A microfluidics device according to claim 1, wherein the plurality of microcantilevers is provided in a planar array of fingers.

6. A microcantilever platform cartridge comprising:
   a plurality of interaction cells, each of the interaction cells including an inlet for receiving a sample fluid, wherein each of the interaction cells receives a different sample fluid, and the interaction cells and inlets are disposed within a housing of the cartridge; and
   a plurality of identically configured microcantilevers disposed in each of the interaction cells, the plurality of microcantilevers disposed in an individual interaction cell capable of deflecting in response to chemical interaction with the same component of the sample fluid.

7. An apparatus for performing microfluidics analysis, the apparatus comprising:
   a housing, the housing comprising a plurality of fluid lines, each of the fluid lines including an inlet for receiving a fluid from a fluid pump, and a plurality of control lines in communication with the fluid lines, each of the control lines including an inlet for receiving a control fluid;
   a microcantilever platform, the microcantilever platform comprising: a plurality of interaction cells, each of the interaction cells including an inlet for receiving one or more preparation fluids and a sample fluid, wherein each of the interaction cells receives a different sample fluid, and an outlet whereby fluid may flow out of the interaction cell, wherein the interaction cells, inlets and outlets are within the housing, and wherein each interaction cell is configured to receive a plurality of identically configured microcantilevers, the plurality of microcantilevers in an individual interaction cell being identically configured to deflect in response to an interaction involving the same component of a sample fluid; and
   a plurality of valves in communication with the fluid lines for selectively controlling the flow of fluid into and out of the interaction cells.

8. An apparatus according to claim 7, and wherein each of the interaction cells further includes a plurality of microcantilevers, each microcantilever within the plurality configured to deflect in response to chemical interactions with a component of the sample fluid.

9. An apparatus according to claim 7, wherein the control fluid lines are adapted to accept a control fluid which is a gas.

10. An apparatus according to claim 7, wherein the number of the plurality of valves is less than the number of the plurality of fluid lines.

11. An apparatus according to claim 7, wherein the number of the plurality of valves is less than the number of the plurality of control lines.

12. An apparatus according to claim 7, further comprising a plurality of expansion chambers for eliminating gas from fluid entering the interaction cells.

13. An apparatus according to claim 7, further comprising a waste receptacle for receiving fluid from the outlets of the interaction cells.

14. An apparatus according to claim 7, further comprising a reservoir for sample collection from each outlet of each interaction cell.

15. An apparatus according to claim 14, wherein at least one of the reservoirs is adapted whereby a sample fluid collected in the adapted reservoir is subject to further analysis.

16. An apparatus according to claim 15, wherein the further analysis includes gel electrophoresis.

17. An apparatus according to claim 16, wherein the gel electrophoresis is multi dimensional.

18. An apparatus according to claim 17, wherein at least one of the dimensions is polyacrylamide gel electrophoresis in the presence of a denaturing detergent.

19. An apparatus according to claim 15, wherein the further analysis includes mass spectroscopy.

20. An apparatus according to claim 7, wherein each of the interaction cells includes a plurality of microcantilevers.

21. An apparatus according to claim 20, wherein the plurality of microcantilevers is provided in a planar array having a plurality of fingers.

22. An apparatus according to claim 7, wherein the apparatus is mounted on a temperature-controlled platform.

23. A microfluidics device cartridge comprising:
   a plurality of interaction cells, each of the interaction cells being configured to receive a plurality of identically configured microcantilevers, wherein each of the microcantilevers in the plurality in each interaction cell is identically configured to deflect in response to a chemical interaction; and
   fluid control means including i) means for providing to the interaction cells a preparation fluid, and ii) means for providing to the interaction cells a sample fluid, wherein each interaction cell receives a different sample fluid.

24. A microfluidics device comprising:
   a housing, the housing comprising a plurality of fluid lines, each of the fluid lines including an inlet for receiving a fluid from a fluid pump disposed within the housing, and a plurality of control lines in communication with the fluid lines, each of the control lines including an inlet for receiving a control fluid;
   a microcantilever platform within the housing, the microcantilever platform comprising a plurality of interaction cells, each of the interaction cells configured to receive a plurality of identically configured microcantilevers, and each of the interaction cells includes an inlet for receiving one or more preparation fluids and a sample fluid, wherein each of the interaction cells receives a different sample fluid, and an outlet whereby fluid may flow out of the interaction cell; and a plurality of valves in communication with the fluid lines for selectively controlling the flow of fluid into and out of the interaction cells.

25. A microfluidics device according to claim 1, wherein the interaction cell further includes at least one outlet whereby fluid flows out of the cell.

26. An apparatus according to claim 7, wherein each of the interaction cells does not include microcantilevers.

* * * * *

UNITED STATES PATENT AND TRADEMARK OFFICE
CERTIFICATE OF CORRECTION

PATENT NO. : 6,926,864 B2
DATED : August 9, 2005
INVENTOR(S) : Peeters et al.

It is certified that error appears in the above-identified patent and that said Letters Patent is hereby corrected as shown below:

Title page,
Insert item -- [73] Assignee: Protiveris, Inc., Rockville, MD --.
Insert item -- [74] *Attorney, Agent or Firm*–Sonia K. Guterman, Lawson & Weitzen, L.L.P. --.

Signed and Sealed this

Eleventh Day of October, 2005

JON W. DUDAS
*Director of the United States Patent and Trademark Office*